United States Patent
Reed et al.

(10) Patent No.: US 9,499,540 B2
(45) Date of Patent: *Nov. 22, 2016

(54) PURIFIED PYRROLOQUINOLINYL-PYRROLIDINE-2,5-DIONE COMPOSITIONS AND METHODS FOR PREPARING AND USING SAME

(71) Applicant: ArQule, Inc., Woburn, MA (US)

(72) Inventors: David P. Reed, Salem, NH (US); Neil R. Barnes, Melrose, MA (US); John C. Kane, West Monroe, NY (US); Christopher A. Lee, Freeville, NY (US); Jian-Xie Chen, Manulis, NY (US); Martin P. Redmon, Oxford, MA (US)

(73) Assignee: ArQule, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/498,651

(22) Filed: Sep. 26, 2014

(65) Prior Publication Data
US 2016/0024076 A1  Jan. 28, 2016

Related U.S. Application Data

(60) Continuation of application No. 14/036,672, filed on Sep. 25, 2013, now Pat. No. 8,871,933, which is a division of application No. 12/975,644, filed on Dec. 22, 2010, now Pat. No. 8,552,192.

(60) Provisional application No. 61/289,563, filed on Dec. 23, 2009.

(51) Int. Cl.
*C07D 471/04* (2006.01)
*C07D 471/06* (2006.01)

(52) U.S. Cl.
CPC ......... *C07D 471/04* (2013.01); *C07D 471/06* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,760,237 A | 6/1998 | Myers | |
| 2003/0229026 A1 | 12/2003 | Al-Awar et al. | |
| 2006/0223760 A1* | 10/2006 | Li | C07D 471/06 514/233.2 |
| 2013/0281699 A1 | 10/2013 | Nakamura et al. | |

FOREIGN PATENT DOCUMENTS

| | | |
|---|---|---|
| WO | 2009002807 | 12/2008 |
| WO | WO 2009/002806 A1 | 12/2008 |

OTHER PUBLICATIONS

Beviglia et al. "Expression of the c-Met/HGF Receptor in Human Breast Carcinoma: Correlation with Tumor Progression", Int. J. Cancer, 74.3(1997):301-309.
Bhattacharya et al. "Thermoanalytical and Crystallographic Methods", Polymorphism in Pharmaceutical Solids, New york: Informa Helathcare, Brittain, er. Chapter 9 (2009):318-335.
CAS Registry No. 102280-97-7, Retrieved Mar. 17, 2011.
CAS Registry No. 879-37-8, Retrieved Mar. 17, 2011.
Danilkovitch-Miagkova et al. "Dysregulation of Met Receptor Tyrosine Kinase Activity in Invasive Tumors", J. Clin. Invest. 109(2002): 863-867.
Ivanisevic et al. "Uses of X-Ray Powder Diffraction in the Pharmaceutical Industry", Pharmaceutical Formulation & Quality, (2011):30-33.
Ma et al. "c-Met:Structure, Functions and Potential for Therapeutic Inhibition", Cancer Metastasis Rev. 22.4 (2003):309-325.
Qian et al. "Met Protein Expression Level Correlates with Survival in Patients with Late-Stage Nasopharyngeal Carcinoma", Cancer Research 62(2002):589-596.
Qiao et al. "Constitutive Activation of Met Kinase in Non-Small-Cell Lung Carcinomas Correlates with Anchorage-Independent Cell Survival", J. Cell. Biochem. 86. 4(2002):665-677.
Takeuchi et al. "c-Met Expression Level in Primary Colon Cancer: A Predictor of Tumor Invasion and Lymph Node Metastases", Clin. Cancer Research 9.4(2003):1480-1488.
Zhang et al. "Met Decoys: Will Cancer Take the Bait?" Cancer Cell. 6.(2004):5-6.
Byrn S. et. al. "Pharmaceutical Solids: A Strategic Approach to Regulatory Considerations", Pharmaceutical research, vol. 12, No. 7. p. 945-954 (1995).

\* cited by examiner

*Primary Examiner* — Timothy R Rozof
(74) *Attorney, Agent, or Firm* — Cooley LLP; Matthew Pavao; Chen Chen

(57) ABSTRACT

The present invention relates to a (±)-trans-3-(5,6-dihydro-4H-pyrrolo[3,2,1-ij]quinolin-1-yl)-4-(1H-indol-3-yl)pyrrolidine-2,5-dione dichloromethane.

5 Claims, 17 Drawing Sheets

(±)-cis-3-(5,6-dihydro-4H-pyrrolo [3,2,1-ij] quinolin-1yl)-4(1H-indol-3-yl) pyrrolidine-2, 5-dione (±)-trans-3-(5,6-dihydro-4H-pyrrolo [3,2,1-ij] quinolin-1-yl)-4(1H-indol-3-yl) pyrrolidine-2, 5-dione.

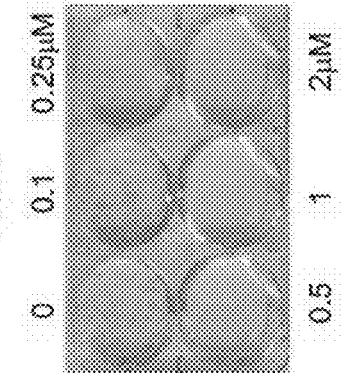
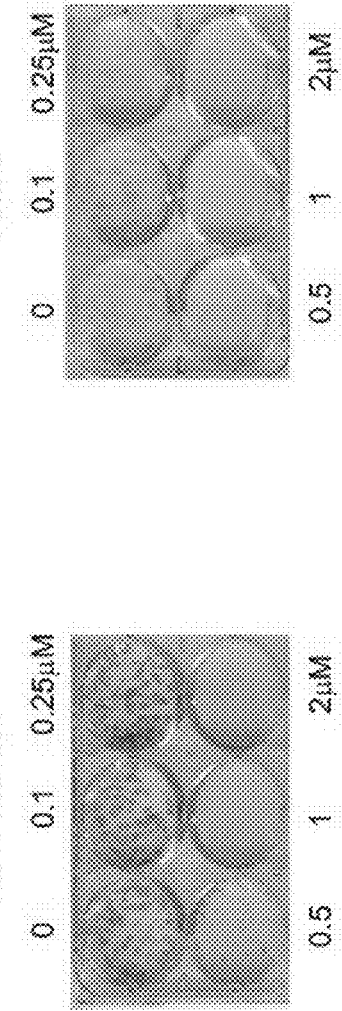
Figure 2A
Figure 2B
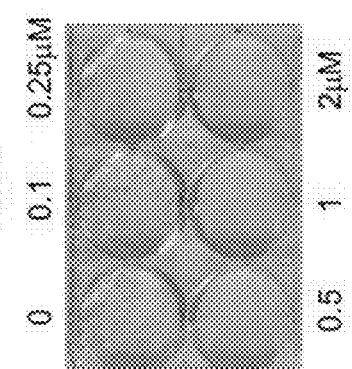
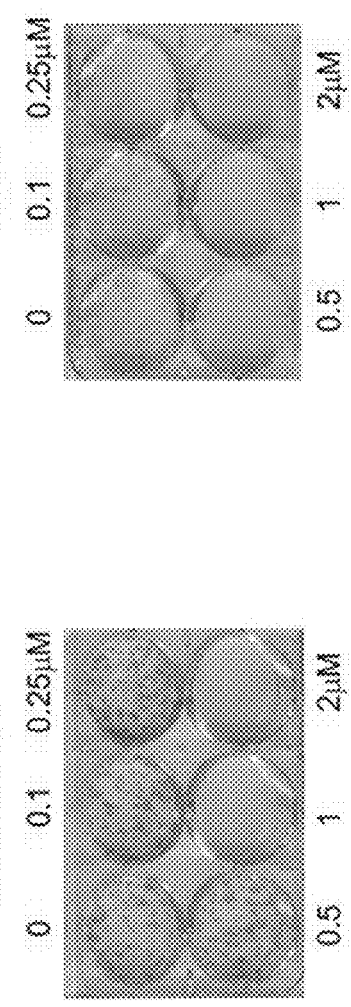
Figure 2C
Figure 2D

A= (-)-trans-3-(5,6-dihydro-4H-pyrrolo [3,2,1-ij] quinolin-1-yl)-4-(1H-indol-3-yl) pyrrolidine-2, 5-dione B= (+)-trans-3-(5,6-dihydro-4H-pyrrolo [3,2,1-ij] quinolin-1-yl)-4-(1H-indol-3-yl) pyrrolidine-2, 5-dione A = (-)-trans-3-(5,6-dihydro-4H-pyrrolo[3,2,1-ij]quinolin-1-yl)-4-(1H-indol-3-yl)pyrrolidine-2,5-dione

PURIFIED PYRROLOQUINOLINYL-PYRROLIDINE-2,5-DIONE COMPOSITIONS AND METHODS FOR PREPARING AND USING SAME

CROSS-REFERENCE TO RELATED APPLICATIONS

This application is a continuation application of U.S. Ser. No. 14/036,672, filed on Sep. 25, 2013, allowed, which is a divisional application of U.S. Ser. No. 12/975,644, filed on Dec. 22, 2010, now U.S. Pat. No. 8,552,192, which claims priority to, and the benefit of, U.S. Ser. No. 61/289,563, filed on Dec. 23, 2009, the contents of each of which are incorporated herein by reference in their entirety.

BACKGROUND OF THE INVENTION

Cancer is the second leading cause of death in the United States, exceeded only by heart disease. (*Cancer Facts and Figures* 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same type that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine,* 5th Edition, Bast et al. eds., B.C. Decker Inc., Hamilton, Ontario)

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are expressed in numerous tissues, and their expression is normally confined predominantly to cells of epithelial and mesenchymal origin, respectively. c-Met and HGF are dysregulated in human cancers and may contribute to dysregulation of cell growth, tumor cell dissemination, and tumor invasion during disease progression and metastasis (See, e.g., *Journal of Clinical Investigation* 109: 863-867 (2002) and *Cancer Cell* pp 5-6 July 2004). c-Met and HGF are highly expressed relative to surrounding tissue in numerous cancers, and their expression correlates with poor prognosis and lack of response to standard clinical treatments. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)). Without intending to be bound by theory, c-Met and HGF may protect tumors against cell death induced by DNA-damaging agents and, as such, may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003)). Accordingly, new compounds and methods for modulating these factors and treating cancer are needed. The present invention addresses these needs.

SUMMARY OF THE INVENTION

The present invention provides a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation. In some embodiments, the polymorph can also be characterized by an X-ray powder diffraction pattern comprising peaks at approximately 8.2, 10.8, 14.1, 15.5, 17.8, 19.9 and 25.6° 2θ using Cu Kα radiation. In other embodiments, the polymorph can also be characterized by an X-ray powder diffraction pattern comprising peaks at approximately 8.2, 10.8, 14.1, 14.9, 15.5, 17.1, 17.8, 19.4, 19.9, 21.1, 21.9, 23.0, 25.6 and 28.4° 2θ using Cu Kα radiation.

The present invention also provides a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation. In some embodiments, the polymorph can also be characterized by an X-ray powder diffraction pattern comprising peaks at approximately 6.5, 9.9, 12.0, 16.7, 20.1 and 22.8° 2θ using Cu Kα radiation. In other embodiments, the polymorph can also be characterized by an X-ray powder diffraction pattern comprising peaks at approximately 6.5, 9.9, 12.0, 13.2, 16.4, 16.7, 17.2, 20.1, 20.3, 20.8, 22.8, 23.7, 28.6 and 30.4° 2θ using Cu Kα radiation.

The present invention also provides a (±)-trans-3-(5,6-dihydro-4H-pyrrolo[3,2,1-ij]quinolin-1-yl)-4-(1H-indol-3-yl)pyrrolidine-2,5-dione dichloromethane and a composition comprising (±)-trans-3-(5,6-dihydro-4H-pyrrolo[3,2,1-ij]quinolin-1-yl)-4-(1H-indol-3-yl)pyrrolidine-2,5-dione dichloromethane. The composition can comprise greater than 90%, greater than 95% or greater than 99% (±)-trans-3-(5,6-dihydro-4H-pyrrolo[3,2,1-ij]quinolin-1-yl)-4-(1H-indol-3-yl)pyrrolidine-2,5-dione dichloromethane.

The present invention also provides a (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine or a composition comprising (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine. The composition can comprise greater than 90%, greater than 95% or greater than 99% (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine. In some embodiments, the composition can comprise less than 1%, less than 0.5% or less than 0.1%

(+)-trans-3-(5,6-dihydro-4H-pyrrolo[3,2,1-ij]quinolin-1-yl)-4-(1H-indol-3-yl)pyrrolidine-2,5-dione pseudoephedrine.

The present invention also provides a chirally purified (−)-trans-3-(5,6-dihydro-4H-pyrrolo[3,2,1-ij]quinolin-1-yl)-4-(1H-indol-3-yl)pyrrolidine-2,5-dione comprising less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising: (a) mixing (±)-trans-3-(5,6-dihydro-4H-pyrrolo[3,2,1-ij]quinolin-1-yl)-4-(1H-indol-3-yl)pyrrolidine-2,5-dione with (1S,2S)-(+)-pseudoephedrine in a first solvent to form solid (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine; (b) washing the (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine solid formed in step (a) with an aqueous mixture of the first solvent; (c) reacting the (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine from step (b) with an acid in an organic solvent and isolating the organic layer of the resultant solution; (d) washing the organic layer from step (c); (e) adding a second solvent to the organic layer; (f) concentrating the organic layer until the amount of the second solvent in the solution is less than 5%; and (g) crystallizing from the organic layer in step (f) and drying the resultant (−)-trans-3-(5,6-dihydro-4H-pyrrolo[3,2,1-ij]quinolin-1-yl)-4-(1H-indol-3-yl)pyrrolidine-2,5-dione solution under vacuum, thereby producing (−)-trans-3-(5,6-dihydro-4H-pyrrolo[3,2,1-ij]quinolin-1-yl)-4-(1H-indol-3-yl)pyrrolidine-2,5-dione.

Preferably, the produced (−)-trans-3-(5,6-dihydro-4H-pyrrolo[3,2,1-ij]quinolin-1-yl)-4-(1H-indol-3-yl)pyrrolidine-2,5-dione comprises less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

The first solvent can be a non-aqueous solvent. Preferably, the first non-aqueous solvent can be methanol, ethanol, cyclohexylethylamine, acetonitrile, or a mixture thereof. The second solvent can be a non-aqueous solvent. Preferably, the second non-aqueous solvent can be methanol, ethanol, acetonitrile, or a mixture thereof. In some embodiments, the second solvent is the same as said first solvent. In other embodiments, the second solvent is different from said first solvent. The organic solvent in step (c) can be methyltetrahydrofuran. In some embodiments, the organic layer is washed with a salt solution in step (d). Preferably, the salt solution is a sodium chloride solution.

The method can further include rinsing (−)-trans-3-(5,6-dihydro-4H-pyrrolo[3,2,1-ij]quinolin-1-yl)-4-(1H-indol-3-yl)pyrrolidine-2,5-dione crystal after step (g). In some embodiments, the (−)-trans-3-(5,6-dihydro-4H-pyrrolo[3,2,1-ij]quinolin-1-yl)-4-(1H-indol-3-yl)pyrrolidine-2,5-dione crystal is rinsed with an alcohol. Preferably, the alcohol is selected from ethanol and methanol.

The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising (a) mixing (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine and an acid; (b) adding an alcohol to the mixture from (a) to form a slurry; (c) heating and stirring the slurry formed in (b); (d) cooling and isolating (−)-trans-3-(5,6-dihydro-4H-pyrrolo[3,2,1-ij]quinolin-1-yl)-4-(1H-indol-3-yl)pyrrolidine-2,5-dione; (e) washing (−)-trans-3-(5,6-dihydro-4H-pyrrolo[3,2,1-ij]quinolin-1-yl)-4-(1H-indol-3-yl)pyrrolidine-2,5-dione isolated in step (d) with a first solvent; (f) dissolving (−)-trans-3-(5,6-dihydro-4H-pyrrolo[3,2,1-ij]quinolin-1-yl)-4-(1H-indol-3-yl)pyrrolidine-2,5-dione from step (e) in a second solvent to form a solution; (g) adding a third solvent to the solution in (f) and distilling the solution until the amount of said second solvent in the solution is less than 5%; (h) crystallizing (−)-trans-3-(5,6-dihydro-4H-pyrrolo[3,2,1-ij]quinolin-1-yl)-4-(1H-indol-3-yl)pyrrolidine-2,5-dione from the solution in (g); (i) optionally, adding a fourth solvent (preferably water) to mature the crystals from (h); (j) isolating the crystals from (i) by filtration; (k) washing the crystals from (j) with a mixture of the third solvent and fourth solvent; and (l) drying the crystals from (k) under vacuum, thereby producing (−)-trans-3-(5,6-dihydro-4H-pyrrolo[3,2,1-ij]quinolin-1-yl)-4-(1H-indol-3-yl)pyrrolidine-2,5-dione.

Preferably, the produced (−)-trans-3-(5,6-dihydro-4H-pyrrolo[3,2,1-ij]quinolin-1-yl)-4-(1H-indol-3-yl)pyrrolidine-2,5-dione comprises less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

The alcohol can be methanol, ethanol, or a mixture thereof. The first solvent can be a non-aqueous solvent. Preferably, the first non-aqueous solvent can be methanol, ethanol, or a mixture thereof. The second solvent can be a non-aqueous solvent. Preferably, the second non-aqueous solvent is tetrahydrofuran. The third solvent can be a non-aqueous solvent. Preferably, the third non-aqueous solvent can be methanol, ethanol, or a mixture thereof.

The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising: (a) dissolving (±)-trans-3-(5,6-dihydro-4H-pyrrolo[3,2,1-ij]quinolin-1-yl)-4-(1H-indol-3-yl)pyrrolidine-2,5-dione in dichloromethane and isolating the (±)-trans-3-(5,6-dihydro-4H-pyrrolo[3,2,1-ij]quinolin-1-yl)-4-(1H-indol-3-yl)pyrrolidine-2,5-dione dichloromethane; (b) dissolving (±)-trans-3-(5,6-dihydro-4H-pyrrolo[3,2,1-ij]quinolin-1-yl)-4-(1H-indol-3-yl)pyrrolidine-2,5-dione dichloromethane in a first solvent; (c) distilling the solution of step (b) until the level of dichloromethane in the solution is <0.1% by weight; (d) diluting the solution of step (c) in a second solvent; (e) introducing the solution of step (d) into a multicolumn chromatography system containing a packing suitable for chiral separation; (f) pooling the resultant raffinate obtained from the system in step (e); and (g) crystallizing the raffinate from step (f) and filtering the resultant (−)-trans-3-(5,6-dihydro-4H-pyrrolo[3,2,1-ij]quinolin-1-yl)-4-(1H-indol-3-yl)pyrrolidine-2,5-dione or evaporating the raffinate from step (f) to dryness, thereby producing (−)-trans-3-(5,6-dihydro-4H-pyrrolo[3,2,1-ij]quinolin-1-yl)-4-(1H-indol-3-yl)pyrrolidine-2,5-dione.

Preferably, the produced (−)-trans-3-(5,6-dihydro-4H-pyrrolo[3,2,1-ij]quinolin-1-yl)-4-(1H-indol-3-yl)pyrrolidine-2,5-dione comprises less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

Preferably, the first non-aqueous solvent can be methanol, ethanol, or a mixture thereof. The second solvent can be a non-aqueous solvent. Preferably, the second non-aqueous solvent can be methanol, ethanol, acetonitrile, or a mixture thereof. More preferably, the second non-aqueous solvent is a mixture of methanol and acetonitrile.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents, and other references mentioned herein are incorporated by reference. The references cited herein are not admitted to be prior art to the claimed invention. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE FIGURES

FIGS. 2A, 2B, 2C, and 2D set forth an effect of (±)-cis-3-(5,6-dihydro-4H-pyrrolo[3,2,1-ij]quinolin-1-yl)-4-(1H-indol-3-yl)pyrrolidine-2,5-dione (FIGS. 2C and 2D) or (±)-trans-3-(5,6-dihydro-4H-pyrrolo[3,2,1-ij]quinolin-1-yl)-4-(1H-indol-3-yl)pyrrolidine-2,5-dione (FIGS. 2A and 2B) on survival of MDA-MB-231 or Paca-2 cells in vitro.

DETAILED DESCRIPTION OF THE INVENTION

Pyrroloquinolinyl-Pyrrolidine-2,5-Dione Compounds

Figure 1A:
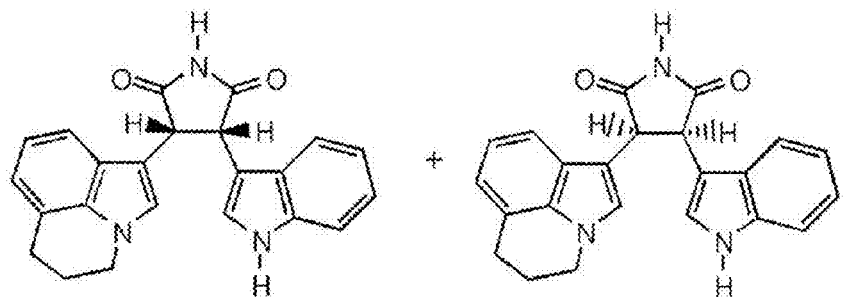
FIGS. 1A and 1B set forth the chemical structures of (±)-cis-3-(5,6-dihydro-4H-pyrrolo[3,2,1-ij]quinolin-1-yl)-4-(1H-indol-3-yl)pyrrolidine-2,5-dione (FIG. 1A) and (±)-trans-3-(5,6-dihydro-4H-pyrrolo[3,2,1-ij]quinolin-1-yl)-4-(1H-indol-3-yl)pyrrolidine-2,5-dione (FIG. 1B).
Figure 1B:
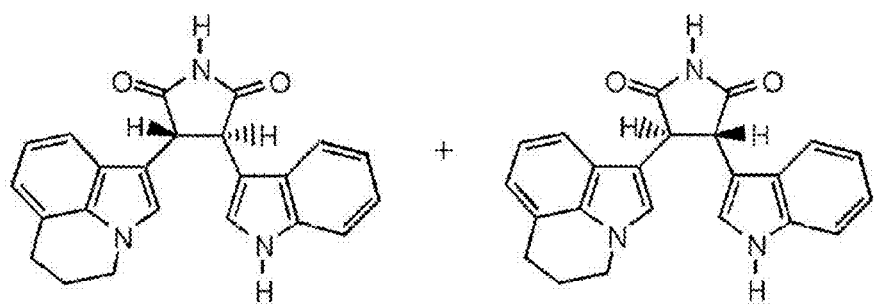

The present invention provides (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione.

The present invention also provides a composition comprising (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione. The composition can comprise one or more pharmaceutically acceptable carriers or excipients.

Preferably, the highly purified (−)-trans-3-(5,6-dihydro-4H-pyrrolo[3,2,1-ij]quinolin-1-yl)-4-(1H-indol-3-yl)pyrrolidine-2,5-dione provided by the instant invention has a chiral purity greater than 99.3%, greater than 99.5%, greater than 99.6%, greater than 99.7%, greater than 99.8% or greater than 99.9%. Preferably, the compositions containing highly purified (−)-trans-3-(5,6-dihydro-4H-pyrrolo[3,2,1-ij]quinolin-1-yl)-4-(1H-indol-3-yl)pyrrolidine-2,5-dione provided by the instant invention contain less than 0.7%, less than 0.5%, less than 0.4%, less than 0.3%, less than 0.2% or less than 0.1% (+)-trans-3-(5,6-dihydro-4H-pyrrolo[3,2,1-ij]quinolin-1-yl)-4-(1H-indol-3-yl)pyrrolidine-2,5-dione.

All forms of the compounds of the instant invention are contemplated, either in admixture or in pure or substantially pure form, including crystalline forms of racemic mixtures and crystalline forms of individual isomers. The invention very particularly embraces isolated optical isomers having a specified activity. The racemic forms can be resolved by physical methods, such as, for example, separation or crystallization of diastereomeric derivatives, separation by chiral column chromatography or supercritical fluid chromatography. The individual optical isomers can be obtained from the racemates by conventional methods, such as, for example, salt formation with an optically active acid or base followed by crystallization.

Certain compounds of this invention may exist in tautomeric forms. All such tautomeric forms of the compounds are considered to be within the scope of this invention unless otherwise stated.

In addition, a crystal polymorphism may be present but is not limiting, but any crystal form may be single or a crystal form mixture, or an anhydrous or hydrated crystal form.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectra, melting points, density, crystal shape, optical and electrical properties, stability and solubility. Crystallization solvent, rate of crystallization, storage temperature, and other factors may cause one crystal form to dominate. Crystal polymorphs of the compounds can be prepared by crystallization under different conditions.

The present invention provides two polymorphs of (−)-trans-3-(5,6-dihydro-4H-pyrrolo[3,2,1-ij]quinolin-1-yl)-4-(1H-indol-3-yl)pyrrolidine-2,5-dione.

A form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation. In some embodiments, the polymorph can also be characterized by an X-ray powder diffraction pattern comprising peaks at approximately 8.2, 10.8, 14.1, 15.5, 17.8, 19.9 and 25.6° 2θ using Cu Kα radiation. In other embodiments, the polymorph can also be characterized by an X-ray powder diffraction pattern comprising peaks at approximately 8.2, 10.8, 14.1, 14.9, 15.5, 17.1, 17.8, 19.4, 19.9, 21.1, 21.9, 23.0, 25.6 and 28.4° 2θ using Cu Kα radiation.

The present invention also provides a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation. In some embodiments, the polymorph can also be characterized by an X-ray powder diffraction pattern comprising peaks at approximately 6.5, 9.9, 12.0, 16.7, 20.1 and 22.8° 2θ using Cu Kα radiation. In other embodiments, the polymorph can also be characterized by an X-ray powder diffraction pattern comprising peaks at approximately 6.5, 9.9, 12.0, 13.2, 16.4, 16.7, 17.2, 20.1, 20.3, 20.8, 22.8, 23.7, 28.6 and 30.4° 2θ using Cu Kα radiation.

The present invention also provides a composition comprising the form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation. The composition can comprise one or more pharmaceutically acceptable carriers or excipients.

The present invention also provides a composition comprising the form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation. The composition can comprise one or more pharmaceutically acceptable carriers or excipients.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The present invention also provides a (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine. The (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine can comprise less than 1% (+)-trans-3-(5,6-dihydro-4H-pyrrolo[3,2,1-ij]quinolin-1-yl)-4-(1H-indol-3-yl)pyrrolidine-2,5-dione pseudoephedrine.

The present invention also provides a composition comprising (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione pseudoephedrine. The composition can comprise one or more pharmaceutically acceptable carriers or excipients.

Preferably, the highly purified (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine provided by the instant invention have a diastereomeric purity greater than 99.5%, greater than 99.6%, greater than 99.7%, greater than 99.8% or greater than 99.9%. Preferably, the compositions containing highly purified (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine provided by the instant invention contain less than 0.5%, less than 0.4%, less than 0.3%, less than 0.2% or less than 0.1% (+)-trans-3-(5,6-dihydro-4H-pyrrolo[3,2,1-ij]quinolin-1-yl)-4-(1H-indol-3-yl)pyrrolidine-2,5-dione pseudoephedrine.

"Solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. For example, the solvate may be a dichloromethane (DCM) solvate.

The present invention also provides a (±)-trans-3-(5,6-dihydro-4H-pyrrolo[3,2,1-ij]quinolin-1-yl)-4-(1H-indol-3-yl)pyrrolidine-2,5-dione dichloromethane and a composition comprising (±)-trans-3-(5,6-dihydro-4H-pyrrolo[3,2,1-ij]quinolin-1-yl)-4-(1H-indol-3-yl)pyrrolidine-2,5-dione dichloromethane. The composition can comprise greater than 90%, greater than 95% or greater than 99% (±)-trans-3-(5,6-dihydro-4H-pyrrolo[3,2,1-ij]quinolin-1-yl)-4-(1H-indol-3-yl)pyrrolidine-2,5-dione dichloromethane. The composition can comprise one or more pharmaceutically acceptable carriers or excipients.

Some compounds of the present invention can exist in a tautomeric form which are also intended to be encompassed within the scope of the present invention. "Tautomers" refers to compounds whose structures differ markedly in arrangement of atoms, but which exist in easy and rapid equilibrium. It is to be understood that the compounds of the invention may be depicted as different tautomers. It should also be understood that when compounds have tautomeric forms, all tautomeric forms are intended to be within the scope of the invention, and the naming of the compounds does not exclude any tautomeric form.

The compounds, salts and prodrugs of the present invention can exist in several tautomeric forms, and such tautomeric forms are included within the scope of the present invention. Tautomers exist as mixtures of a tautomeric set in solution. In solid form, usually one tautomer predominates. Even though one tautomer may be described, the present invention includes all tautomers of the present compounds As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts.

As used herein, the term "metabolite" means a product of metabolism of a compound of the present invention, or a pharmaceutically acceptable salt, polymorph or solvate thereof, that exhibits a similar activity in vivo to said compound of the present invention.

As used herein, the term "mixing" means combining, blending, stirring, shaking, swirling or agitating. The term "stirring" means mixing, shaking, agitating, or swirling. The term "agitating" means mixing, shaking, stirring, or swirling.

The compounds of the present invention can also be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. The term "prodrug" includes a compound of the present invention covalently linked to one or more pro-moieties, such as an amino acid moiety or other water-solubilizing moiety. A compound of the present invention may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, the pro-moiety, e.g., an amino acid moiety or other water solubilizing moiety such as phosphate may be selected based on solubility, stability, bioavailability, and/or in vivo delivery or uptake. The term "prodrug" is also intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxy, or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elesevier, New York-Oxford (1985).

Synthesis of (−)-trans-3-(5,6-dihydro-4H-pyrrolo[3,2,1-ij]quinolin-1-yl)-4-(1H-indol-3-yl)pyrrolidine-2,5-dione Compounds Standard synthetic methods and procedures for the preparation of organic molecules and functional group transformations and manipulations, including the use of protective groups, can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. The following descriptions of synthetic methods are designed to illustrate, but not limit, general procedures for the preparation of compounds of the invention.

The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising: (a) mixing (±)-trans-3-(5,6-dihydro-4H-pyrrolo[3,2,1-ij]quinolin-1-yl)-4-(1H-indol-3-yl)pyrrolidine-2,5-dione with (1S,2S)-(+)-pseudoephedrine in a first solvent to form solid (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine; (b) washing the (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine solid formed in step (a) with an aqueous mixture of the first solvent; (c) reacting the (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine from step (b) with an acid in an organic solvent and isolating the organic layer of the resultant solution; (d) washing the organic layer from step (c); (e) adding a second solvent to the organic layer; (f) concentrating the organic layer until the amount of the second solvent in the solution is less than 5%; and (g) crystallizing from the organic layer in step (f) and drying the resultant (−)-trans-3-(5,6-dihydro-4H-pyrrolo[3,2,1-ij]quinolin-1-yl)-4-(1H-indol-3-yl)pyrrolidine-2,5-dione under vacuum, thereby producing (−)-trans-3-(5,6-dihydro-4H-pyrrolo[3,2,1-ij]quinolin-1-yl)-4-(1H-indol-3-yl)pyrrolidine-2,5-dione. Preferably, the produced (−)-trans-3-(5,6-dihydro-4H-pyrrolo[3,2,1-ij]quinolin-1-yl)-4-(1H-indol-3-yl)pyrrolidine-2,5-dione comprises less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

The first solvent can be a non-aqueous solvent. Preferably, the first non-aqueous solvent can be methanol, ethanol, acetonitrile, or a mixture thereof. The second solvent can be a non-aqueous solvent. Preferably, the second non-aqueous solvent can be methanol, ethanol, acetonitrile, or a mixture thereof. In some embodiments, the second solvent is the same as said first solvent. In other embodiments, the second solvent is different from said first solvent. The organic solvent in step (c) can be methyltetrahydrofuran. In some embodiments, the organic layer is washed with a salt solution in step (d). Preferably, the salt solution is a sodium chloride solution.

The method can further include rinsing (−)-trans-3-(5,6-dihydro-4H-pyrrolo[3,2,1-ij]quinolin-1-yl)-4-(1H-indol-3-yl)pyrrolidine-2,5-dione crystal after step (g). In some embodiments, the (−)-trans-3-(5,6-dihydro-4H-pyrrolo[3,2,1-ij]quinolin-1-yl)-4-(1H-indol-3-yl)pyrrolidine-2,5-dione crystal is rinsed with an alcohol. Preferably, the alcohol is selected from ethanol and methanol.

The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising (a) mixing (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine and an acid; (b) adding an alcohol to the mixture from (a) to form a slurry; (c) heating and stirring the slurry formed in (b); (d) cooling and isolating (−)-trans-3-(5,6-dihydro-4H-pyrrolo[3,2,1-ij]quinolin-1-yl)-4-(1H-indol-3-yl)pyrrolidine-2,5-dione; (e) washing (−)-trans-3-(5,6-dihydro-4H-pyrrolo[3,2,1-ij]quinolin-1-yl)-4-(1H-indol-3-yl)pyrrolidine-2,5-dione isolated in step (d) with a first solvent; (f) dissolving (−)-trans-3-(5,6-dihydro-4H-pyrrolo[3,2,1-ij]quinolin-1-yl)-4-(1H-indol-3-yl)pyrrolidine-2,5-dione from step (e) in a second solvent to form a solution; (g) adding a third solvent to the solution in (f) and distilling the solution until the amount of said second solvent in the solution is less than 5%; (h) crystallizing (−)-trans-3-(5,6-dihydro-4H-pyrrolo[3,2,1-ij]quinolin-1-yl)-4-(1H-indol-3-yl)pyrrolidine-2,5-dione from the solution in (g); (i) optionally, adding a fourth solvent (preferably water) to mature the crystals from (h); (j) isolating the crystals from (i) by filtration; (k) washing the crystals from (j) with a mixture of the third solvent and fourth solvent; and (l) drying the crystals from (k) under vacuum, thereby producing (−)-trans-3-(5,6-dihydro-4H-pyrrolo[3,2,1-ij]quinolin-1-yl)-4-(1H-indol-3-yl)pyrrolidine-2,5-dione.

The alcohol can be methanol, ethanol, or a mixture thereof. The first solvent can be a non-aqueous solvent. Preferably, the first non-aqueous solvent can be methanol, ethanol, or a mixture thereof. The second solvent can be a non-aqueous solvent. Preferably, the second non-aqueous solvent is tetrahydrofuran. The third solvent can be a non-aqueous solvent. Preferably, the third non-aqueous solvent can be methanol, ethanol, or a mixture thereof. The fourth solvent can be an aqueous solvent. Preferably, the fourth solvent is water. The present invention also provides a method for preparing (−)-trans-3-(5,6-dihydro-4H-pyrrolo[3,2,1-ij]quinolin-1-yl)-4-(1H-indol-3-yl)pyrrolidine-2,5-dione, comprising: (a) dissolving (±)-trans-3-(5,6-dihydro-4H-pyrrolo[3,2,1-ij]quinolin-1-yl)-4-(1H-indol-3-yl)pyrrolidine-2,5-dione in dichloromethane and isolating the (±)-trans-3-(5,6-dihydro-4H-pyrrolo[3,2,1-ij]quinolin-1-yl)-4-(1H-indol-3-yl)pyrrolidine-2,5-dione dichloromethane; (b) dissolving (±)-trans-3-(5,6-dihydro-4H-pyrrolo[3,2,1-ij]quinolin-1-yl)-4-(1H-indol-3-yl)pyrrolidine-2,5-dione dichloromethane in a first solvent; (c) distilling the solution of step (b) until the level of dichloromethane in the solution is <0.1% by weight; (d) diluting the solution of step (c) in a second solvent; (e) introducing the solution of step (d) into a multicolumn chromatography system containing a packing suitable for chiral separation; (f) pooling the resultant raffinate obtained from the system in step (e); and (g) crystallizing the raffinate from step (f) and filtering the resultant (−)-trans-3-(5,6-dihydro-4H-pyrrolo[3,2,1-ij]quinolin-1-yl)-4-(1H-indol-3-yl)pyrrolidine-2,5-dione or evaporating the raffinate from step (f) to dryness, thereby producing (−)-trans-3-(5,6-dihydro-4H-pyrrolo[3,2,1-ij]quinolin-1-yl)-4-(1H-indol-3-yl)pyrrolidine-2,5-dione. Preferably, the produced (−)-trans-3-(5,6-dihydro-4H-pyrrolo[3,2,1-ij]quinolin-1-yl)-4-(1H-indol-3-yl)pyrrolidine-2,5-dione comprises less than 1%, less than 0.7%, less than 0.5% or less than 0.1% (+)-trans-3-(5,6-dihydro-4H-pyrrolo[3,2,1-ij]quinolin-1-yl)-4-(1H-indol-3-yl)pyrrolidine-2,5-dione.

Preferably, the first non-aqueous solvent can be methanol, ethanol, or a mixture thereof. The second solvent can be a non-aqueous solvent. Preferably, the second non-aqueous solvent can be methanol, ethanol, acetonitrile, or a mixture thereof. More preferably, the second non-aqueous solvent is a mixture of methanol and acetonitrile.

Scheme I provides a summary for the production of the instant compositions comprising highly purified (>99% chiral purity) (−)-trans-3-(5,6-dihydro-4H-pyrrolo[3,2,1-ij]quinolin-1-yl)-4-(1H-indol-3-yl)pyrrolidine-2,5-dione, with minimal amounts (<1%) of the undesired enantiomer, (+)-trans-3-(5,6-dihydro-4H-pyrrolo[3,2,1-ij]quinolin-1-yl)-4-(1H-indol-3-yl)pyrrolidine-2,5-dione, present. Preferably, the compositions comprise (−)-trans-3-(5,6-dihydro-4H-pyrrolo[3,2,1-ij]quinolin-1-yl)-4-(1H-indol-3-yl)pyrrolidine-2,5-dione having a chiral purity greater than 99.3%, greater than 99.5%, greater than 99.6%, greater than 99.7%, greater than 99.8% or greater than 99.9%. Preferably, the compositions comprise less than 0.7%, less than 0.5%, less than 0.4%, less than 0.3%, less than 0.2% or less than 0.1% (+)-trans-3-(5,6-dihydro-4H-pyrrolo[3,2,1-ij]quinolin-1-yl)-4-(1H-indol-3-yl)pyrrolidine-2,5-dione.

As shown in scheme I and described in detail in the following examples, various procedures are utilized to produce and isolate these compositions comprising highly chirally pure (−)-trans-3-(5,6-dihydro-4H-pyrrolo[3,2,1-ij]quinolin-1-yl)-4-(1H-indol-3-yl)pyrrolidine-2,5-dione, including but not limited to, multicolumn chromatography resolution, diastereomeric salt resolution or dynamic kinetic resolution.

In step 1 of scheme I, lilolidine (Compound 4), was treated with oxalylchloride to give the acyl chloride in methyl tert-butyl ether (MTBE) reaction solvent. The addition of methanol was sufficient to afford the intermediate ketoester, 5,6-dihydro-4H-pyrrolo[3,2,1-ij]quinolin-1-yl)oxoacetic acid methyl ester (Compound 5). In Step 2 of the reaction, Compound 5 and indole-3-acetamide (Compound 5a) were combined to produce 3-(5,6-dihydro-4H-pyrrolo[3,2,1-ij]quinolin-1-yl)-4-(1H-indol-3-yl)pyrrole-2,5-dione (Compound 6). As described in detail in the following examples, it is not necessary to isolate intermediate Compound 5 to produce Compound 6. A solvent swap from MTBE into tetrahydrofuran (THF) was necessary prior to conducting Step 2, since both 5 and 5a have very poor solubility in MTBE. Following the addition of Compound 5a to consume Compound 5 in THF in the presence of base, HCl was added to complete the reaction to afford crude Compound 6. Crude Compound 6 was then purified from DCM and heptane to afford Compound 6 of sufficient purity to proceed to the next step. A detailed description of this process is shown in Example 1.

Compound 6 was hydrogenated with palladium hydroxide, THF, and potassium tert-butoxide to produce crude trans racemate, (±)-trans-3-(5,6-dihydro-4H-pyrrolo[3,2,1-ij]quinolin-1-yl)-4-(1H-indol-3-yl)pyrrolidine-2,5-dione (Compound 8). As described in the examples, the preparation of Compound 8, does not require the isolation of crude cis racemate (±)-cis-3-(5,6-dihydro-4H-pyrrolo[3,2,1-ij]quinolin-1-yl)-4-(1H-indol-3-yl)pyrrolidine-2,5-dione (Compound 7). Rather, during the hydrogenation of Compound 6, conditions were modified to effect the isomerization of the resultant Compound 7 in situ.

The resulting process provides a means to control key impurities in Compound 8, specifically Compound 6. Specifically, the reaction is carried out in THF solvent, and the catalyst employed is palladium hydroxide. Potassium tert-butoxide is also added to the reaction mixture to promote the isomerization. A detailed description of this process is shown in Example 2.

The most common impurity in Compound 8 is typically Compound 7. Since Compound 7 is itself chiral, it is particularly difficult to predict the elution of isomers of Compound 7 from Multicolumn Chromatography (MCC) when lower purity (<99%) Compound 8 is utilized. In order to ensure high purity product, it is, therefore, necessary to increase the purity of the racemate, Compound 8, prior to enantiomeric resolution by MCC. It was determined that the purity of Compound 8 could be improved through selective crystallization of solvates from various solvents. One such solvate formed from dichloromethane (DCM) yields Compound 8 DCM with very high chemical purity (>99%). As shown in scheme I, the Compound 8 DCM was formed by dissolving the crude Compound 8 in DCM and then seeding with DCM crystals. After growing the seed bed to a critical mass, heptane was added to drive the crystallization to completion. After isolation by filtration and removal of bulk residual solvent under vacuum, Compound 8 DCM typically contained 0.8-0.9 moles of DCM with respect to Compound 8. This solvate crystallization removes the process impurities present in crude (95-98%) Compound 8 as a result of the hydrogenation and isomerization. A detailed description of this process is shown in Example 3.

The present invention provides the chiral resolution of the two enantiomers of Compound 8 DCM by MCC, as shown in Scheme I. The MCC enantiomeric separation process provides an advantage over separation by HPLC batch chromatography in that it can provide high chiral purity (>99%) on larger scale (>20 kg) than batch preparation. MCC resolution can be carried out in either methanol, a mixture of methanol and ethanol (1:1 vol) or methanol and acetonitrile (9:1 v/v). The chiral stationary phase (CSP) utilized is either Chiralpak AD or AZ purchased from Chiral Technologies, Inc. The concentration of the racemate feed solution is in the range of 20-50 g/L. Preferably, the specified chiral purity for the separation is >99% of (−)-trans-3-(5,6-dihydro-4H-pyrrolo[3,2,1-ij]quinolin-1-yl)-4-(1H-indol-3-yl)pyrrolidine-2,5-dione (Compound 10) and containing <1% of (+)-trans-3-(5,6-dihydro-4H-pyrrolo[3,2,1-ij]quinolin-1-yl)-4-(1H-indol-3-yl)pyrrolidine-2,5-dione (Compound 9).

Specifically, separations are carried out by preparing a feed solution of racemic Compound 8 in the chosen mobile phase. This solution is prepared from Compound 8 DCM by initially dissolving the material in methanol. The chromatographic parameters were estimated prior to production, and final optimization was conducted during the initial hours or days of separation of the feed solution. Where initial fractions collected did not meet the chiral purity specification, the material was recycled into the feed solution to repeat the resolution. Once the operating parameters to meet specifications had been established, the conditions were applied to separate the entire volume of feed solution. Throughout the operation, Compound 10 was collected as the raffinate stream, pooled, and concentrated. The concentrated raffinate was then either concentrated to dryness (<5 kg scale) or concentrated and seeded to induce crystallization of Compound 10 (>5 kg scale). A detailed description of this process is shown in Example 4.

In addition to MCC resolution, a classical approach for the resolution of chiral acids or bases through the formation of diastereomeric salts has been employed. In the case of Compound 10, either acids or bases could be used, since the molecule is amphoteric. Following a detailed screen of chiral bases, it was shown that the salts formed from the enatiomers of Compound 8 with pseudoephedrine have vastly different solubility profiles in some solvents. This relationship was optimized to allow for the resolution of Compound 8 using (1S,2S)-(+)-pseudoephedrine to afford (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine (Compound 10.(1S,2S)-(+)-pseudoephedrine) selectively. A detailed description of this process is shown in Example 6. Another process provided by the instant invention is to racemize the undesired enantiomer, (+)-trans-3-(5,6-dihydro-4H-pyrrolo[3,2,1-ij]quinolin-1-yl)-4-(1H-indol-3-yl)pyrrolidine-2,5-dione (Compound 9), in situ using Dynamic Kinetic Resolution (DKR). A detailed description of this process is shown in Example 7.

In both the MCC resolution and classical diastereomeric salt resolution process, the undesired enantiomer, Compound 9, is isolated. This undesired enantiomer can be isomerized to obtain racemic Compound 8. This is accomplished by implementing the same procedure for isomerizing the cis-isomer, Compound 7, to afford crude trans racemate Compound 8. The isomerization is carried out in either methanol or ethanol using sodium hydroxide as a base. A detailed description of this process is shown in Example 5.

The synthesis methods described in Scheme I are readily reproducible on a large scale, e.g., 10 kg, 20 kg, 30 kg, 40 kg, 50 kg, and 60 kg and higher providing an overall yield of >45% of (−)-trans-3-(5,6-dihydro-4H-pyrrolo[3,2,1-ij]quinolin-1-yl)-4-(1H-indol-3-yl)pyrrolidine-2,5-dione (Compound 10), based on indole acetamide as a limiting reagent. Preferably, 1 kg of lilolidine (Compound 4) yields approximately 1 kg of (−)-trans-3-(5,6-dihydro-4H-pyrrolo[3,2,1-ij]quinolin-1-yl)-4-(1H-indol-3-yl)pyrrolidine-2,5-dione (Compound 10) having a purity >99%.

The present invention also provides a method to prepare polymorphs of (−)-trans-3-(5,6-dihydro-4H-pyrrolo[3,2,1-ij]quinolin-1-yl)-4-(1H-indol-3-yl)pyrrolidine-2,5-dione. The crude Compound 10 was dissolved in a solvent, for example, THF, by heating the resulting mixture to 50° C. The resulting mixture was polish filtered, followed by the addition of a second solvent, such as methanol, and a Form 1 seed crystal of Compound 10.

The use of seed crystals imparts polymorphic control of the crystallization process. In the absence of seeding, either Form 1 or Form 2 can be spontaneously crystallized in high purity. Thus, to provide Form 1 or Form 2 seeds, spontaneous crystallization is permitted; and once formed, the crystalline product can be characterized using quantitative analysis by x-ray powder diffraction to determine the resulting crystal form and its polymorphic purity. Following such characterization, this crystalline product can be used as "seed crystals" or "seeds" to control the polymorph, either Form 1 or Form 2, generated during the subsequent crystallizations as described herein.

The solution was then concentrated azeotropically and atmospherically by distillation to reduce the volume of the solvent, e.g., THF. The temperature of the solution was reduced to 50° C. and stirred for at least 4 hours. Aliquots were removed to confirm to formation of the desired polymorph. If required, the polymorph can be redissolved in THF (30% of batch volume), polish filtered, concentrated and seeded to obtain the desired polymorphic outcome. When the desired polymorphic form was obtained, a solution of 50% aqueous methanol was added at 50° C. and the solution was agitated for an additional 2-3 hours. The solution was then cooled to ambient temperature and held for at least 2 hours to allow crystallization. Upon completion, the crystals were isolated by filtration, washed with additional 50% aqueous methanol, and dried under vacuum at 65° C. for at least 12 hours. Polymorphic Form 1 of Compound 10 was isolated as a red-brown solid.

Form 2 polymorph of (−)-trans-3-(5,6-dihydro-4H-pyrrolo[3,2,1-ij]quinolin-1-yl)-4-(1H-indol-3-yl)pyrrolidine-2,5-dione can also be prepared with the above method if the Form 1 seed crystal is replaced by the Form 2 seed crystal.

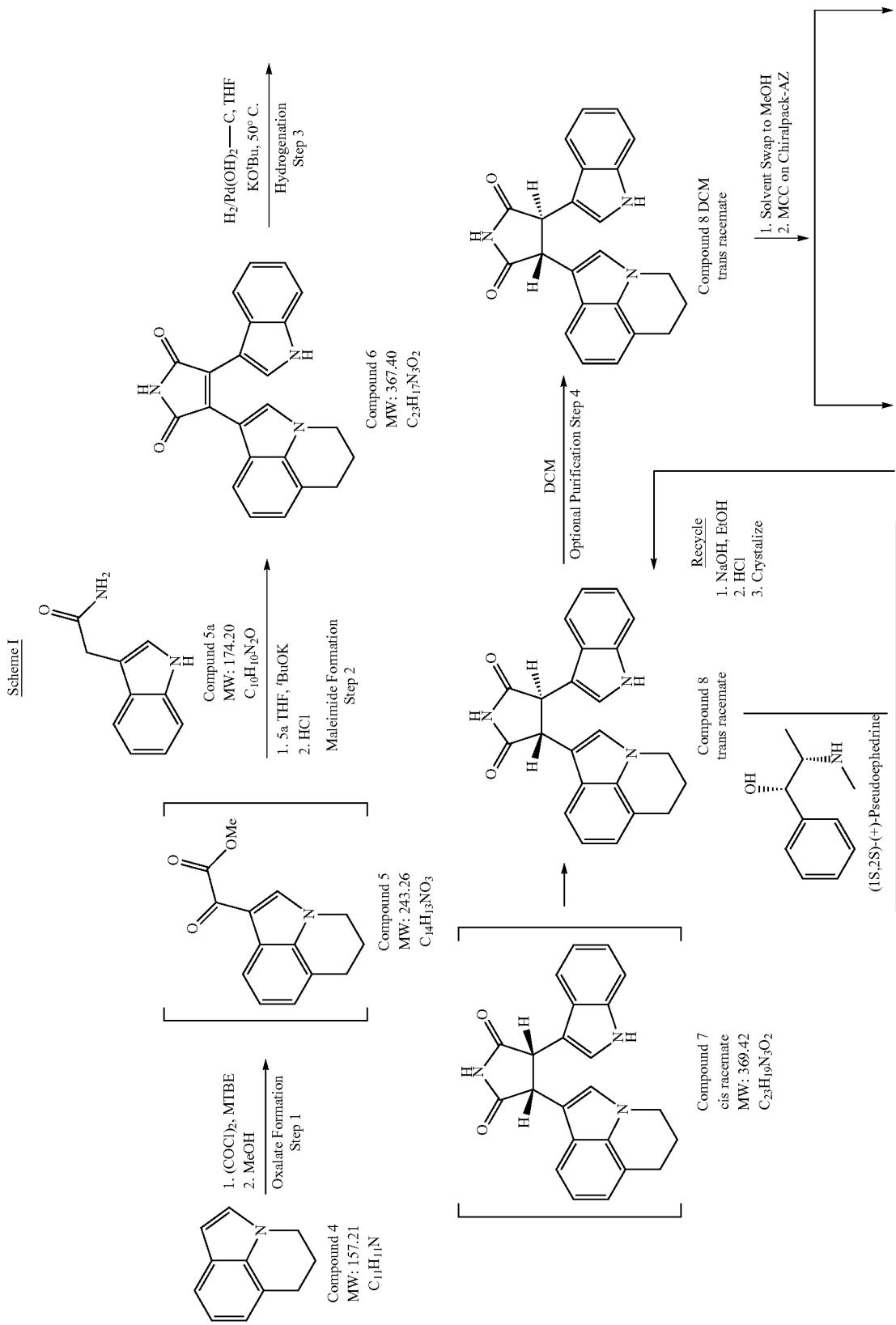

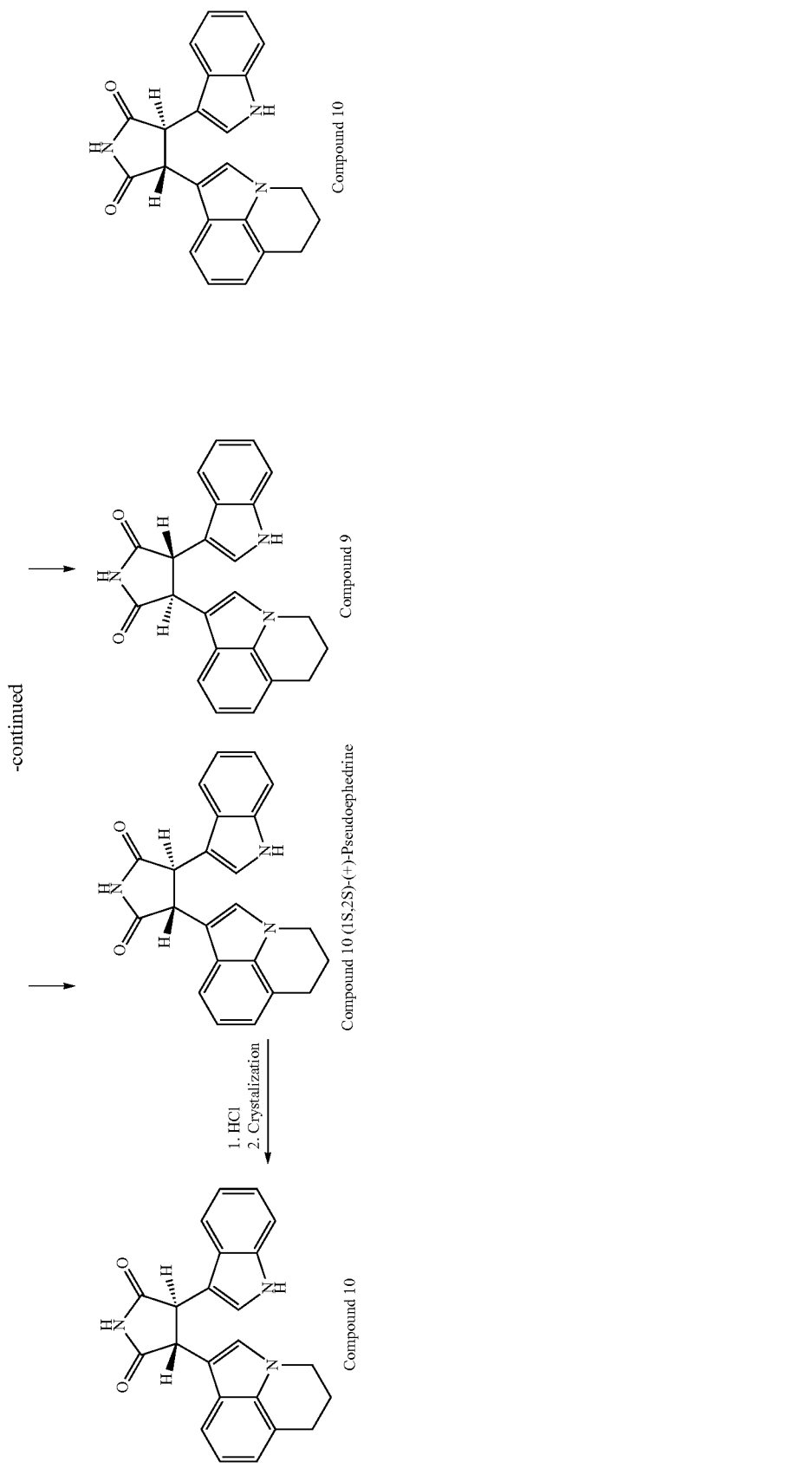

Methods of Treatment

The present invention provides methods for the treatment of a cell proliferative disorder in a subject in need thereof by administering to a subject in need of such treatment, a therapeutically effective amount of a pharmaceutical composition comprising (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients.

The cell proliferative disorder can be cancer or a precancerous condition. The present invention further provides the use of a composition of (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients for the preparation of a medicament useful for the treatment of a cell proliferative disorder.

The present invention also provides methods of protecting against a cell proliferative disorder in a subject in need thereof by administering a therapeutically effective amount of a pharmaceutical composition comprising (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients, and one or more pharmaceutically acceptable carriers or excipients to a subject in need of such treatment. The cell proliferative disorder can be cancer or a precancerous condition. The present invention also provides the use of a compound of (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients. for the preparation of a medicament useful for protecting against a cell proliferative disorder.

As used herein, a "subject in need thereof" is a subject having a cell proliferative disorder, or a subject having an increased risk of developing a cell proliferative disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, the term "cell proliferative disorder" refers to conditions in which unregulated or abnormal growth, or both, of cells can lead to the development of an unwanted condition or disease, which may or may not be cancerous. Exemplary cell proliferative disorders of the invention encompass a variety of conditions wherein cell division is deregulated. Exemplary cell proliferative disorder include, but are not limited to, neoplasms, benign tumors, malignant tumors, pre-cancerous conditions, in situ tumors, encapsulated tumors, metastatic tumors, liquid tumors, solid tumors, immunological tumors, hematological tumors, cancers, carcinomas, leukemias, lymphomas, sarcomas, and rapidly dividing cells. The term "rapidly dividing cell" as used herein is defined as any cell that divides at a rate that exceeds or is greater than what is expected or observed among neighboring or juxtaposed cells within the same tissue. A cell proliferative disorder includes a precancer or a precancerous condition. A cell proliferative disorder includes cancer. Preferably, the methods provided herein are used to treat or alleviate a symptom of cancer. The term "cancer" includes solid tumors, as well as, hematologic tumors and/or malignancies. A "precancer cell" or "precancerous cell" is a cell manifesting a cell proliferative disorder that is a precancer or a precancerous condition. A "cancer cell" or "cancerous cell" is a cell manifesting a cell proliferative disorder that is a cancer. Any reproducible means of measurement may be used to identify cancer cells or precancerous cells. Cancer cells or precancerous cells can be identified by histological typing or grading of a tissue sample (e.g., a biopsy sample). Cancer cells or precancerous cells can be identified through the use of appropriate molecular markers.

Exemplary non-cancerous conditions or disorders include, but are not limited to, rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus.

Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

A "cell proliferative disorder of the hematologic system" is a cell proliferative disorder involving cells of the hematologic system. A cell proliferative disorder of the hematologic system can include lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. A cell proliferative disorder of the hematologic system can include hyperplasia, dysplasia, and metaplasia of cells of the hematologic system. Preferably, compositions of the present invention may be used to treat a cancer selected from the group consisting of a hematologic cancer of the present invention or a hematologic cell proliferative disorder of the present invention. A hematologic cancer of the present invention can include multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. Cell proliferative disorders of the lung can include all forms of cell proliferative disorders affecting lung cells. Cell proliferative disorders of the lung can include lung cancer, a precancer or precancerous condition of the lung, benign growths or lesions of the lung, and malignant growths or lesions of the lung, and metastatic lesions in tissue and organs in the body other than the lung. Preferably, compositions of the present invention may be used to treat lung cancer or cell proliferative disorders of the lung. Lung cancer can include all forms of cancer of the lung. Lung cancer can include malignant lung neoplasms, carcinoma in situ, typical carcinoid tumors, and atypical carcinoid tumors. Lung cancer can include small cell lung cancer ("SCLC"), non-small cell lung cancer ("NSCLC"), non-squamous non-small cell lung cancer, squamous non-small cell lung cancer, squamous cell carcinoma, non-squamous cell carcinoma, adenocarcinoma, small cell carcinoma, large cell carcinoma, adenosquamous cell carcinoma, and mesothelioma. Lung cancer can include "scar carcinoma," bronchioalveolar carcinoma, giant cell carcinoma, spindle cell carcinoma, and large cell neuroendocrine carcinoma. Lung cancer can include lung neoplasms having histologic and ultrastructual heterogeneity (e.g., mixed cell types).

Cell proliferative disorders of the lung can include all forms of cell proliferative disorders affecting lung cells. Cell proliferative disorders of the lung can include lung cancer, precancerous conditions of the lung. Cell proliferative disorders of the lung can include hyperplasia, metaplasia, and dysplasia of the lung. Cell proliferative disorders of the lung can include asbestos-induced hyperplasia, squamous metaplasia, and benign reactive mesothelial metaplasia. Cell proliferative disorders of the lung can include replacement of columnar epithelium with stratified squamous epithelium, and mucosal dysplasia. Individuals exposed to inhaled injurious environmental agents such as cigarette smoke and asbestos may be at increased risk for developing cell proliferative disorders of the lung. Prior lung diseases that may predispose individuals to development of cell proliferative disorders of the lung can include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. Preferably, the cell proliferative disorder of the colon is colon cancer. Preferably, compositions of the present invention may be used to treat colon cancer or cell proliferative disorders of the colon. Colon cancer can include all forms of cancer of the colon. Colon cancer can include sporadic and hereditary colon cancers. Colon cancer can include malignant colon neoplasms, carcinoma in situ, typical carcinoid tumors, and atypical carcinoid tumors. Colon cancer can include adenocarcinoma, squamous cell carcinoma, and adenosquamous cell carcinoma. Colon cancer can be associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. Colon cancer can be caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

Cell proliferative disorders of the colon can include all forms of cell proliferative disorders affecting colon cells. Cell proliferative disorders of the colon can include colon cancer, precancerous conditions of the colon, adenomatous polyps of the colon and metachronous lesions of the colon. A cell proliferative disorder of the colon can include adenoma. Cell proliferative disorders of the colon can be characterized by hyperplasia, metaplasia, and dysplasia of the colon. Prior colon diseases that may predispose individuals to development of cell proliferative disorders of the colon can include prior colon cancer. Current disease that may predispose individuals to development of cell proliferative disorders of the colon can include Crohn's disease and ulcerative colitis. A cell proliferative disorder of the colon can be associated with a mutation in a gene selected from the group consisting of p53, ras, FAP and DCC. An individual can have an elevated risk of developing a cell proliferative disorder of the colon due to the presence of a mutation in a gene selected from the group consisting of p53, ras, FAP and DCC.

A "cell proliferative disorder of the prostate" is a cell proliferative disorder involving cells of the prostate. Cell proliferative disorders of the prostate can include all forms of cell proliferative disorders affecting prostate cells. Cell proliferative disorders of the prostate can include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate can include hyperplasia, metaplasia, and dysplasia of the prostate.

A "cell proliferative disorder of the skin" is a cell proliferative disorder involving cells of the skin. Cell proliferative disorders of the skin can include all forms of cell proliferative disorders affecting skin cells. Cell proliferative disorders of the skin can include a precancer or precancerous condition of the skin, benign growths or lesions of the skin, melanoma, malignant melanoma and other malignant growths or lesions of the skin, and metastatic lesions in tissue and organs in the body other than the skin. Cell proliferative disorders of the skin can include hyperplasia, metaplasia, and dysplasia of the skin.

A "cell proliferative disorder of the ovary" is a cell proliferative disorder involving cells of the ovary. Cell proliferative disorders of the ovary can include all forms of cell proliferative disorders affecting cells of the ovary. Cell proliferative disorders of the ovary can include a precancer or precancerous condition of the ovary, benign growths or lesions of the ovary, ovarian cancer, malignant growths or lesions of the ovary, and metastatic lesions in tissue and organs in the body other than the ovary. Cell proliferative disorders of the skin can include hyperplasia, metaplasia, and dysplasia of cells of the ovary.

A "cell proliferative disorder of the breast" is a cell proliferative disorder involving cells of the breast. Cell proliferative disorders of the breast can include all forms of cell proliferative disorders affecting breast cells. Cell proliferative disorders of the breast can include breast cancer, a precancer or precancerous condition of the breast, benign growths or lesions of the breast, and malignant growths or lesions of the breast, and metastatic lesions in tissue and organs in the body other than the breast. Cell proliferative disorders of the breast can include hyperplasia, metaplasia, and dysplasia of the breast.

A cell proliferative disorder of the breast can be a precancerous condition of the breast. Compositions of the present invention may be used to treat a precancerous condition of the breast. A precancerous condition of the breast can include atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). A precancerous condition of the breast can be staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

The cell proliferative disorder of the breast can be breast cancer. Preferably, compositions of the present invention may be used to treat breast cancer. Breast cancer includes all forms of cancer of the breast. Breast cancer can include primary epithelial breast cancers. Breast cancer can include cancers in which the breast is involved by other tumors such as lymphoma, sarcoma or melanoma. Breast cancer can include carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. Breast cancer can include Stage I, II, IIIA, IIIB, IIIC and IV breast cancer. Ductal carcinoma of the breast can include invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. Lobular carcinoma of the breast can include invasive lobular carcinoma with predominant in situ component, invasive lobular carcinoma, and infiltrating lobular carcinoma. Breast cancer can include Paget's disease, Paget's disease with intraductal carcinoma, and Paget's disease with invasive ductal carcinoma. Breast cancer can include breast neoplasms having histologic and ultrastructual heterogeneity (e.g., mixed cell types).

Preferably, a compound of the present invention may be used to treat breast cancer. A breast cancer that is to be treated can include familial breast cancer. A breast cancer that is to be treated can include sporadic breast cancer. A breast cancer that is to be treated can arise in a male subject. A breast cancer that is to be treated can arise in a female subject. A breast cancer that is to be treated can arise in a premenopausal female subject or a postmenopausal female subject. A breast cancer that is to be treated can arise in a subject equal to or older than 30 years old, or a subject younger than 30 years old. A breast cancer that is to be treated has arisen in a subject equal to or older than 50 years old, or a subject younger than 50 years old. A breast cancer that is to be treated can arise in a subject equal to or older than 70 years old, or a subject younger than 70 years old.

A breast cancer that is to be treated can be typed to identify a familial or spontaneous mutation in BRCA1, BRCA2, or p53. A breast cancer that is to be treated can be typed as having a HER2/neu gene amplification, as overexpressing HER2/neu, or as having a low, intermediate or high level of HER2/neu expression. A breast cancer that is to be treated can be typed for a marker selected from the group consisting of estrogen receptor (ER), progesterone receptor (PR), human epidermal growth factor receptor-2, Ki-67, CA15-3, CA 27-29, and c-Met. A breast cancer that is to be treated can be typed as ER-unknown, ER-rich or ER-poor. A breast cancer that is to be treated can be typed as ER-negative or ER-positive. ER-typing of a breast cancer may be performed by any reproducible means. ER-typing of a breast cancer may be performed as set forth in Onkologie 27: 175-179 (2004). A breast cancer that is to be treated can be typed as PR-unknown, PR-rich or PR-poor. A breast cancer that is to be treated can be typed as PR-negative or PR-positive. A breast cancer that is to be treated can be typed as receptor positive or receptor negative. A breast cancer that is to be treated can be typed as being associated with elevated blood levels of CA 15-3, or CA 27-29, or both.

A breast cancer that is to be treated can include a localized tumor of the breast. A breast cancer that is to be treated can include a tumor of the breast that is associated with a negative sentinel lymph node (SLN) biopsy. A breast cancer that is to be treated can include a tumor of the breast that is associated with a positive sentinel lymph node (SLN) biopsy. A breast cancer that is to be treated can include a tumor of the breast that is associated with one or more positive axillary lymph nodes, where the axillary lymph nodes have been staged by any applicable method. A breast cancer that is to be treated can include a tumor of the breast that has been typed as having nodal negative status (e.g., node-negative) or nodal positive status (e.g., node-positive). A breast cancer that is to be treated can include a tumor of the breast that has metastasized to other locations in the body. A breast cancer that is to be treated can be classified as having metastasized to a location selected from the group consisting of bone, lung, liver, or brain. A breast cancer that is to be treated can be classified according to a characteristic selected from the group consisting of metastatic, localized, regional, local-regional, locally advanced, distant, multicentric, bilateral, ipsilateral, contralateral, newly diagnosed, recurrent, and inoperable.

A compound of the present invention may be used to treat or prevent a cell proliferative disorder of the breast, or to treat or prevent breast cancer, in a subject having an increased risk of developing breast cancer relative to the population at large. A subject with an increased risk of developing breast cancer relative to the population at large is a female subject with a family history or personal history of breast cancer. A subject with an increased risk of developing breast cancer relative to the population at large is a female subject having a germ-line or spontaneous mutation in BRCA1 or BRCA2, or both. A subject with an increased risk of developing breast cancer relative to the population at large is a female subject with a family history of breast cancer and a germ-line or spontaneous mutation in BRCA1 or BRCA2, or both. A subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. A subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

A breast cancer that is to be treated can histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. A breast cancer that is to be treated can be assigned a tumor grade according to the International Consensus Panel on the Treatment of Breast Cancer selected from the group consisting of grade 1, grade 1-2, grade 2, grade 2-3, or grade 3.

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1 (mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder." A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention that has been or will be tested in one or more in vitro or in vivo biological assays, in order to determine if that compound is likely to elicit a desired biological or medical response in a cell, tissue, system, animal or human that is being sought by a researcher or clinician. A candidate compound is a pharmaceutical composition comprising (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients. The biological or medical response can be the treatment of cancer. The biological or medical response can be treatment or prevention of a cell proliferative disorder. In vitro or in vivo biological assays can include, but are not limited to, enzymatic activity assays, electrophoretic mobility shift assays, reporter gene assays, in vitro cell viability assays, and the assays described herein.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, prodrug, metabolite, polymorph or solvate thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention is more effective than combination therapy in inducing a desired biological effect.

As used herein, "treating" or "treat" describes the management and care of a patient for the purpose of combating a disease, condition, or disorder and includes the administration of a compound of the present invention to alleviate the symptoms or complications of a disease, condition or disorder, or to eliminate the disease, condition or disorder.

The compounds of the present invention can also be used to prevent a disease, condition or disorder. As used herein, "preventing" or "prevent" describes reducing or eliminating the onset of the symptoms or complications of the disease, condition or disorder.

Treating cancer can result in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, prodrug, metabolite, polymorph or solvate thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, prodrug, metabolite, polymorph or solvate thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%;

more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "selectively" means tending to occur at a higher frequency in one population than in another population. The compared populations can be cell populations. Preferably, a compound of the present invention, or a pharmaceutically acceptable salt, prodrug, metabolite, polymorph or solvate thereof, acts selectively on a cancer or precancerous cell but not on a normal cell. Preferably, a compound of the present invention, or a pharmaceutically acceptable salt, prodrug, metabolite, polymorph or solvate thereof, acts selectively to modulate one molecular target (e.g., c-met) but does not significantly modulate another molecular target (e.g., Protein Kinase C). The invention also provides a method for selectively inhibiting the activity of an enzyme, such as a kinase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention or a pharmaceutically acceptable salt, prodrug, metabolite, polymorph or solvate thereof, can modulate the activity of a molecular target (e.g., c-met). Modulating refers to stimulating or inhibiting an activity of a molecular target. Preferably, a compound of the present invention modulates the activity of a molecular target if it stimulates or inhibits the activity of the molecular target by at least 2-fold relative to the activity of the molecular target under the same conditions but lacking only the presence of said compound. More preferably, a compound of the present invention modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, prodrug, metabolite, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention demonstrates a minimum of a four fold differential, preferably a ten fold differential, more preferably a fifty fold differential, in the dosage required to achieve a biological effect. Preferably, a compound of the present invention demonstrates this differential across the range of inhibition, and the differential is exemplified at the $IC_{50}$, i.e., a 50% inhibition, for a molecular target of interest.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of a kinase of interest.

The present invention provides methods to assess biological activity of a composition comprising (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than containing less than 1% (+)-trans-3-(5,6-dihydro-4H-pyrrolo[3,2,1-ij]quinolin-1-yl)-4-(1H-indol-3-yl)pyrrolidine-2,5-dione; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation.

In one method, an assay based on enzymatic activity can be utilized. In one specific enzymatic activity assay, the enzymatic activity is from a kinase. As used herein, "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body, and although each of these phosphorylate particular protein/peptide substrates, they all bind the same second substrate ATP in a highly conserved pocket. About 50% of the known oncogene products are protein tyrosine kinases (PTKs), and their kinase activity has been shown to lead to cell formation. Preferably, the kinase assayed is a tyrosine kinase.

A change in enzymatic activity caused by compounds of the present invention can be measured in the disclosed assays. The change in enzymatic activity can be characterized by the change in the extent of phosphorylation of certain substrates. As used herein, "phosphorylation" refers to the addition of phosphate groups to a substrate, including proteins and organic molecules; and, plays an important role in regulating the biological activities of proteins. Preferably, the phosphorylation assayed and measured involves the addition of phosphate groups to tyrosine residues. The substrate can be a peptide or protein.

In some assays, immunological reagents, e.g., antibodies and antigens, are employed. Fluorescence can be utilized in the measurement of enzymatic activity in some assays. As used herein, "fluorescence" refers to a process through which a molecule emits a photon as a result of absorbing an incoming photon of higher energy by the same molecule.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of c-Met. As used herein, an activity of c-Met refers to any biological function or activity that is carried out by c-Met. For example, a function of c-Met includes phosphorylation of downstream target proteins.

Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

Administering a compound of the present invention, or a pharmaceutically acceptable salt, prodrug, metabolite, polymorph or solvate thereof, to a cell or a subject in need thereof can result in modulation (i.e., stimulation or inhibition) of an activity of ERK1 or ERK 2, or both. As used herein, an activity of ERK1 or ERK 2 refers to any biological function or activity that is carried out by ERK1 or ERK 2. For example, a function of ERK1 or ERK 2 includes phosphorylation of downstream target proteins.

Activating refers to placing a composition of matter (e.g., protein or nucleic acid) in a state suitable for carrying out a desired biological function. A composition of matter capable of being activated also has an unactivated state. An activated composition of matter may have an inhibitory or stimulatory biological function, or both.

Elevation refers to an increase in a desired biological activity of a composition of matter (e.g., a protein or a nucleic acid). Elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. A cell cycle checkpoint regulator can be a protein or not a protein.

Treating cancer or a cell proliferative disorder can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., (2003) *Proc Natl Acad Sci USA*. 100(5): 2674-8. In an aspect, cell death occurs by apoptosis.

Preferably, an effective amount of a compound of the present invention, or a pharmaceutically acceptable salt, prodrug, metabolite, polymorph or solvate thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, prodrug, metabolite, polymorph or solvate thereof, can induce or activate cell death selectively in cancer cells. Administering to a subject in need thereof a compound of the present invention, or a pharmaceutically acceptable salt, prodrug, metabolite, polymorph or solvate thereof, can induce or activate cell death selectively in cancer cells. Contacting a cell with a compound of the present invention, or a pharmaceutically acceptable salt, prodrug, metabolite, polymorph or solvate thereof, can induce cell death selectively in one or more cells affected by a cell proliferative disorder. Preferably, administering to a subject in need thereof a compound of the present invention, or a pharmaceutically acceptable salt, prodrug, metabolite, polymorph or solvate thereof, induces cell death selectively in one or more cells affected by a cell proliferative disorder.

The present invention relates to a method of treating or preventing cancer by administering a compound of the present invention, or a pharmaceutically acceptable salt, prodrug, metabolite, polymorph or solvate thereof to a subject in need thereof, where administration of the compound of the present invention, or a pharmaceutically acceptable salt, prodrug, metabolite, polymorph or solvate thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18$^{th}$ edition (1990). These texts can, of course, also be referred to in making or using an aspect of the invention As used herein, "combination therapy" or "co-therapy" includes the administration of a compound of the present invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A compound of the present invention, or a pharmaceutically acceptable salt, prodrug, metabolite, polymorph or solvate thereof, may be administered in combination with a second chemotherapeutic agent. The second chemotherapeutic agent can be a taxane, an aromatase inhibitor, an anthracycline, a microtubule targeting drug, a topoisomerase poison drug, a targeted monoclonal or polyconal antibody, an inhibitor of a molecular target or enzyme (e.g., a kinase inhibitor), or a cytidine analogue drug. Preferably, the chemotherapeutic agent can be, but not restricted to, tamoxifen, raloxifene, anastrozole, exemestane, letrozole, HERCEPTIN® (trastuzumab), GLEEVEC® (imatanib), TAXOL® (paclitaxel), cyclophosphamide, lovastatin, minosine, araC, 5-fluorouracil (5-FU), methotrexate (MTX), TAXOTERE® (docetaxel), ZOLADEX® (goserelin), vincristin, vinblastin, nocodazole, teniposide, etoposide, GEMZAR® (gemcitabine), epothilone, navelbine, camptothecin, daunonibicin, dactinomycin, mitoxantrone, amsacrine, doxorubicin (adriamycin), epirubicin or idarubicin. The second chemotherapeutic agent can be a cytokine such as G-CSF (granulocyte colony stimulating factor). A compound of the present invention, or a pharmaceutically acceptable salt, prodrug, metabolite, polymorph or solvate thereof, may be administered in combination with radiation therapy. A compound of the present invention, or a pharmaceutically acceptable salt, prodrug, metabolite, polymorph or solvate thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone)

A compound of the invention, or a pharmaceutically acceptable salt, prodrug, metabolite, polymorph or solvate thereof, may be administered with an inhibitor of an enzyme, such as a receptor or non-receptor kinase. Receptor and non-receptor kinases of the invention are, for example, tyrosine kinases or serine/threonine kinases. Kinase inhibitors of the invention are small molecules, polynucleic acids, polypeptides, or antibodies.

Exemplary tyrosine kinases include, but are not limited to, Bevacizumab (targets VEGF), BIBW 2992 (targets EGFR and Erb2), Cetuximab/Erbitux (targets Erb1), Imatinib/Gleevec (targets Bcr-Abl), Trastuzumab (targets Erb2), Gefitinib/Iressa (targets EGFR), Ranibizumab (targets VEGF), Pegaptanib (targets VEGF), Erlotinib/Tarceva (targets Erb1), Nilotinib (targets Bcr-Abl), Lapatinib (targets Erb1 and Erb2/Her2), GW-572016/lapatinib ditosylate (targets HER2/Erb2), Panitumumab/Vectibix (targets EGFR), Vandetinib (targets RET/VEGFR), E7080 (multiple targets including RET and VEGFR), Herceptin (targets HER2/Erb2), PKI-166 (targets EGFR), Canertinib/CI-1033 (targets EGFR), Sunitinib/SU-11464/Sutent (targets EGFR and FLT3), Matuzumab/Emd7200 (targets EGFR), EKB-569 (targets EGFR), Zd6474 (targets EGFR and VEGFR), PKC-412 (targets VEGR and FLT3), Vatalanib/Ptk787/ZK222584 (targets VEGR), CEP-701 (targets FLT3), SU5614 (targets FLT3), MLN518 (targets FLT3), XL999 (targets FLT3), VX-322 (targets FLT3), Azd0530 (targets SRC), BMS-354825 (targets SRC), SKI-606 (targets SRC), CP-690 (targets JAK), AG-490 (targets JAK), WHI-P154 (targets JAK), WHI-P131 (targets JAK), Sorafinib/Nexavar (targets RAF kinase, VEGFR-1, VEGFR-2, VEGFR-3, PDGFR-β, KIT, FLT-3, and RET), Dasatinib/Sprycel (BCR/ABL and Src), AC-220 (targets Flt3), AC-480 (targets all HER proteins, "panHER"), Motesanib diphosphate (targets VEGF1-3, PDGFR, and c-kit), Denosumab (targets RANKL, inhibits SRC), AMG888 (targets HER3), and AP24534 (multiple targets including Flt3).

Exemplary serine/threonine kinases include, but are not limited to, Rapamune (targets mTOR/FRAP1), Deforolimus (targets mTOR), Certican/Everolimus (targets mTOR/FRAP1), AP23573 (targets mTOR/FRAP1), Eril/Fasudil hydrochloride (targets RHO), Flavopiridol (targets CDK), Seliciclib/CYC202/Roscovitrine (targets CDK), SNS-032/BMS-387032 (targets CDK), Ruboxistaurin (targets PKC), Pkc412 (targets PKC), Bryostatin (targets PKC), KAI-9803 (targets PKC), SF1126 (targets PI3K), VX-680 (targets Aurora kinase), Azd1152 (targets Aurora kinase), Arry-142886/AZD-6244 (targets MAP/MEK), SCID-469 (targets MAP/MEK), GW681323 (targets MAP/MEK), CC-401 (targets JNK), CEP-1347 (targets JNK), and PD 332991 (targets CDK).

Preferred combinatorial therapies include, but are not limited to, (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients, administered in combination with Erlotinib, (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients administered in combination with gemcitabine, and (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients administered in combination with sorafinib. In certain embodiments, a subject or patient receives a combination of Erlotinib, administered as 150 mg once daily, in combination with (−)-trans-3-(5,6-dihydro-4H-pyrrolo[3,2,1-ij]quinolin-1-yl)-4-(1H-indol-3-yl)pyrrolidine-2,5-dione, administered as 360 mg twice daily.

In other embodiments, a subject or patient receives a combination of gemcitabine, administered by 1000 mg/m² intravenous infusion over 30 minutes once weekly, in combination with (−)-trans-3-(5,6-dihydro-4H-pyrrolo[3,2,1-ij]quinolin-1-yl)-4-(1H-indol-3-yl)pyrrolidine-2,5-dione, administered as 360 mg by mouth twice a day or 120 mg by mouth twice a day continuously. In another embodiment, a subject or patient receives a combination of sorafinib, administered as 200 mg twice daily, in combination with (−)-trans-3-(5,6-dihydro-4H-pyrrolo[3,2,1-ij]quinolin-1-yl)-4-(1H-indol-3-yl)pyrrolidine-2,5-dione, administered as 360 mg twice daily. Preferred dosage forms for (−)-trans-3-(5,6-dihydro-4H-pyrrolo[3,2,1-ij]quinolin-1-yl)-4-(1H-indol-3-yl)pyrrolidine-2,5-dione include, but are not limited to, a capsule and a tablet.

Pharmaceutical Compositions

The present invention also provides pharmaceutical compositions comprising (a) (−)-trans-3-(5,6-dihydro-4H-pyrrolo[3,2,1-ij]quinolin-1-yl)-4-(1H-indol-3-yl)pyrrolidine-2,5-dione having a chiral purity greater than 99% as determined by HPLC and containing less than 1% (+)-trans-3-(5,6-dihydro-4H-pyrrolo[3,2,1-ij]quinolin-1-yl)-4-(1H-indol-3-yl)pyrrolidine-2,5-dione and a pharmaceutically acceptable carrier; (b) a form 1 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 8.2, 10.8 and 14.1° 2θ using Cu Kα radiation, and one or more pharmaceutically acceptable carriers or excipients; or (c) a form 2 polymorph of (−)-trans-3-(5,6-dihydro-4H-pyrrolo[3,2,1-ij]quinolin-1-yl)-4-(1H-indol-3-yl)pyrrolidine-2,5-dione characterized by an X-ray powder diffraction pattern comprising peaks at approximately 6.5, 9.9 and 12.0° 2θ using Cu Kα radiation, and one or more pharmaceutically acceptable carriers or excipients.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, (e.g., intravenous, intradermal, subcutaneous), oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered daily, every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, and/or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch, pregelatinized starch, or lactose, a disintegrating agent such as croscarmellose sodium, sodium starch glycolate, sodium carboxymethyl starch, alginic acid, Primogel, crospovidone, or corn starch; a lubricant such as magnesium stearate, stearic acid, sodium stearyl fumarate, or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser, which contains a suitable propellant, e.g., hydrofluoroalkanes, chlorofluorocarbons, carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid or mixtures or copolymers of polyesters. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). In preferred applications, the dosage can be approximately 400 milligrams twice daily (b.i.d.). In specific applications, the dosage is 360 milligrams (mg) twice daily (b.i.d.). More preferably, dosage form is a capsule or tablet and is administered as two or three capsules or tablets with a combined dosage of 360 milligrams (mg). This dosage form is administered twice daily for a total dose of 720 milligrams (mg). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to recur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compounds of the present invention can also be prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound.

Prodrugs include compounds of the present invention wherein a hydroxyl, amino, sulfhydryl, carboxy or carbonyl group is bonded to any group that, may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, hydroxy, phosphates, sulfates and benzoate derivatives) and carbamates (e.g., N,N-dimethylaminocarbonyl) of hydroxyl functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs*, p 1-92, Elesevier, New York-Oxford (1985).

The compounds, or pharmaceutically acceptable salts, esters or prodrugs thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Techniques for formulation and administration of the disclosed compounds of the invention can be found in *Remington: the Science and Practice of Pharmacy*, 19$^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight.

Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Example 1

The present example describes the preparation of 3-(5,6-dihydro-4H-pyrrolo[3,2,1-ij]quinolin-1-yl)-4-(1H-indol-3-yl)pyrrole-2,5-dione.

Lilolidine [CAS 102280-97-7] (70 kg) (Compound 4 in Scheme I) was charged to an appropriately cleaned and dry reactor vessel followed by methyl tert-butyl ether (MTBE) (375 kg). Lilolidine may be purchased commercially or prepared as described in U.S. Patent Application Publication No. 2006/0223760. The resulting batch was agitated for a minimum of 10 minutes at 15-25° C. A solution of oxalyl chloride (56.6 kg) in MTBE (370 kg) was prepared in a separate vessel. The lilolidine solution was then added to the oxalyl chloride solution at such a rate to maintain the temperature below 32° C. The vessel was rinsed with additional MTBE (162 kg) and added to the reaction mixture. The batch was stirred at 15-32° C. for a minimum of two hours prior to analysis by HPLC. When the reaction was determined to be complete, methanol (90 kg) was added, and the batch was stirred for a minimum of two hours. When the reaction was determined to be complete by HPLC analysis, the batch was distilled to approximately 80 gallons. It is not necessary to isolate the intermediate 5,6-dihydro-4H-pyrrolo[3,2,1-ij]quinolin-1-yl)oxoacetic acid methyl ester (Compound 5 in Scheme I). Tetrahydrofuran (THF) (840 kg) was added to the batch and the volume was again reduced to approximately 80 gallons by distillation. This solvent swap process was continued until the amount of MTBE present in the batch was <1% by weight. A new vessel was charged with indole-3-acetamide [CAS 879-37-8] (61.3 kg) (Compound 5a in Scheme I) followed by THF (840 kg). The resulting solution was then charged to the batch at a rate such that the temperature was maintained at 15-25° C. The vessel containing the solution of indole-3-acetamide was rinsed with THF (140 kg), and the rinse was added to the batch. The empty vessel was then charged with potassium tert-butoxide solution (1.6 M in THF, 581 kg) and THF (350 kg). The solution was also added to the batch, and the resulting solution was stirred at 20-32° C. for a minimum of three hours. When the starting material had been consumed as confirmed by HPLC analysis, aqueous HCl (conc., 273 kg) was added at such a rate that the temperature was maintained below 50° C. The batch was stirred at 40-50° C. for a minimum of 30 minutes.

When the reaction had been determined to be complete by HPLC analysis, aqueous ammonium hydroxide solution (conc.) was added, while maintaining the reaction temperature below 40° C., until the pH of the mixture was 9-10. Following the addition of ethyl acetate (EtOAc) (462 kg) and agitation of the batch, the layers were separated. The organic layer was washed with brine (182 kg NaCl and 1022 kg water). The resulting organic solution was distilled to approximately one third of the starting volume. Ethanol (2B, 1120 kg) was added, and the distillation was continued to reduce the batch volume to approximately 240 gallons. Ethanol (2B, 1120 kg) was again added, and the volume reduced to 240 gallons. Water (1400 kg) was then added to the batch to induce precipitation of the product. The batch was agitated for a minimum of two hours, and the solids were isolated by filtration. The solids were then taken up in dichloromethane (DCM) (840 kg), and heptanes (442 kg) were added to purify the product. Following agitation of the batch for at least two hours, the product was isolated by filtration. Following conditioning on the filter, approximately 115 kg (88%) of 3-(5,6-dihydro-4H-pyrrolo[3,2,1-ij]quinolin-1-yl)-4-(1H-indol-3-yl)pyrrole-2,5-dione (Compound 6 in Scheme I) was isolated as a red powder. This conversion of Compound 4 to Compound 6 is shown in Scheme II.

Scheme II

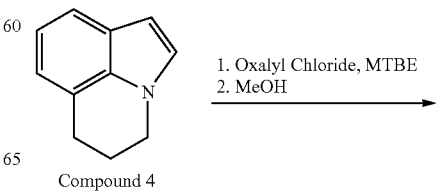

Compound 4

1. Oxalyl Chloride, MTBE
2. MeOH

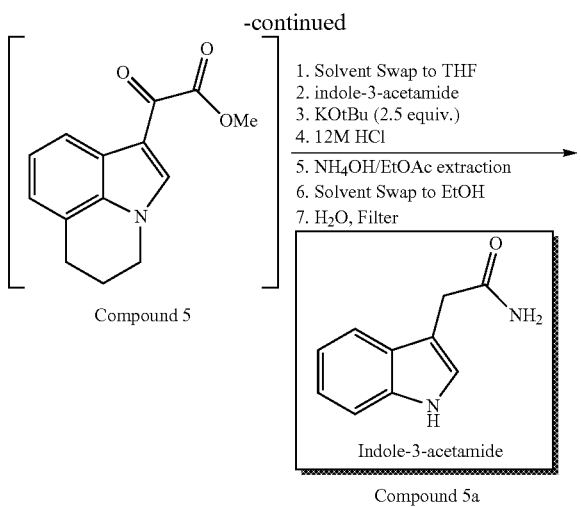

Compound 5

Indole-3-acetamide

Compound 5a

1. Solvent Swap to THF
2. indole-3-acetamide
3. KOtBu (2.5 equiv.)
4. 12M HCl
5. NH₄OH/EtOAc extraction
6. Solvent Swap to EtOH
7. H₂O, Filter

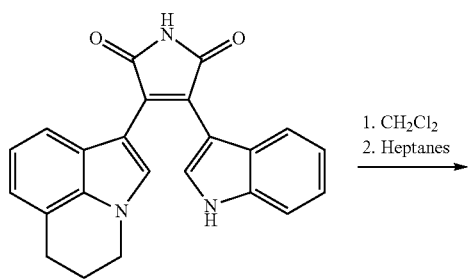

Crude Compound 6 90-92% (HPLC area)

1. CH₂Cl₂
2. Heptanes

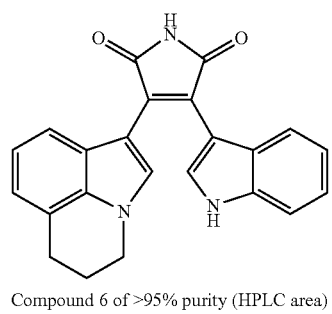

Compound 6 of >95% purity (HPLC area)

Example 2

The present example describes the preparation of (±)-trans-3-(5,6-dihydro-4H-pyrrolo[3,2,1-ij]quinolin-1-yl)-4-(1H-indol-3-yl)pyrrolidine-2,5-dione.

Palladium hydroxide (20 wt % Pd on carbon, 11.5 kg) was charged to a properly prepared reaction vessel. THF (340 kg) was added to produce a slurry, and the catalyst was prereduced with hydrogen (50-75 psi). Compound 6 (115 kg) was charged to an empty vessel followed by THF (353 kg). The resulting mixture was stirred until dissolution was complete. The solution of Compound 6 was then transferred to the slurry of the catalyst. A solution of potassium tert-butoxide (1.6 M in THF, 36 kg) was charged to an empty reactor followed by THF (21 kg). This resulting solution was also transferred to the reaction mixture followed by an additional rinse with THF (340 kg). The batch was then heated to 45-55° C. under 65-80 psi of hydrogen. It is not necessary to isolate the intermediate cis racemate (±)-cis-3-(5,6-dihydro-4H-pyrrolo[3,2,1-ij]quinolin-1-yl)-4-(1H-indol-3-yl)pyrrolidine-2,5-dione (Compound 7 in Scheme I).

When the reaction was determined to be complete by HPLC analysis, the batch was filtered through Celite to remove the catalyst and diluted with isopropylacetate (iPrOAc) (810 kg). The organic solution was washed with aqueous HCl (28 kg conc. HCl, 290 kg water). This process was repeated a second time. The organic solution was then washed with brine (580 kg) prior to being concentrated to approximately 300 gallons by distillation. iPrOAc (1690 kg) was added, and the batch was distilled to approximately 400 gallons. The distillation process was repeated by adding iPrOAc (1000 kg) until the THF content was <2% by weight in the solution. Heptanes (2000 kg) were then added to induce precipitation of the product. The crude (±)-trans-3-(5,6-dihydro-4H-pyrrolo[3,2,1-ij]quinolin-1-yl)-4-(1H-indol-3-yl)pyrrolidine-2,5-dione (Compound 8 in Scheme I) was isolated by filtration and conditioned to afford 111 kg (95%) having an HPLC purity of ~96%. This material also contained 1.7% iPrOAc and 6.3% heptane. This material was confirmed through laboratory scale "use" testing to be of sufficient purity to proceed with preparation of the (±)-trans-3-(5,6-dihydro-4H-pyrrolo[3,2,1-ij]quinolin-1-yl)-4-(1H-indol-3-yl)pyrrolidine-2,5-dione dichloromethane (DCM) and resolution by multicolumn chromatography (MCC) or for direct use in crystallization of the diastereomeric salt, as described in further detail in the following examples.

Example 3

The present example describes preparation of (±)-trans-3-(5,6-dihydro-4H-pyrrolo[3,2,1-ij]quinolin-1-yl)-4-(1H-indol-3-yl)pyrrolidine-2,5-dione DCM.

It is preferred to chemically purify Compound 8 by production of crystalline (±)-trans-3-(5,6-dihydro-4H-pyrrolo[3,2,1-ij]quinolin-1-yl)-4-(1H-indol-3-yl)pyrrolidine-2,5-dione DCM (Compound 8 DCM in Scheme I) prior to the process of enantiomeric resolution by MCC.

In one example, the reaction vessel was charged with methanol (125 kg) and Compound 8 (52.5 kg) and the resulting mixture was heated to 55-65° C. DCM (557 kg) was charged to a clean reactor. The solution of Compound 8 was then transferred to the reactor containing DCM through an inline filter. The reactor was rinsed with DCM (134 kg) which was also transferred through the filter to the reactor containing the reaction mixture. The batch was agitated for a minimum of 30 minutes prior to the introduction of Compound 8 DCM seeds (0.1 kg). The batch was stirred for at least four hours and then sampled to estimate the extent of crystallization. When the filtrate concentration of Compound 8 was below 65 mg/mL, heptanes (718 kg) were added and the batch was stirred for at least one hour. The batch was then cooled to 0-5° C., and the product was isolated by filtration. The solids were conditioned on the filter and dried in a vacuum tray drier at 45-55° C. for at least four hours. Compound 8 DCM (48.3 kg, 92%, HPLC 99.0%) was isolated as a tan solid. The conversion of Compound 6 to Compound 8 DCM described in examples 2 and 3 are shown in Scheme III.

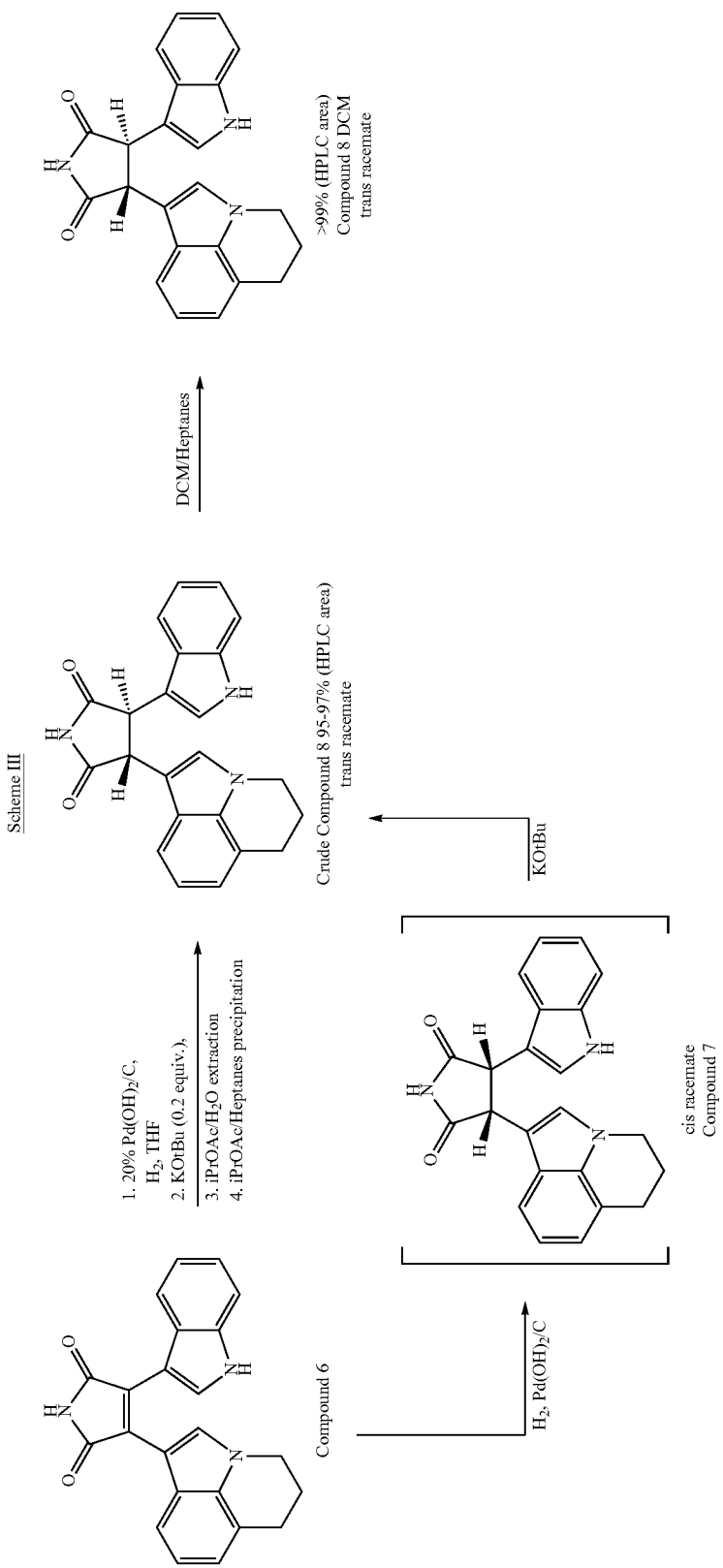

Example 4

The present example describes the chiral resolution of (±)-trans-3-(5,6-dihydro-4H-pyrrolo[3,2,1-ij]quinolin-1-yl)-4-(1H-indol-3-yl)pyrrolidine-2,5-dione DCM by MCC and isolation of (−)-trans-3-(5,6-dihydro-4H-pyrrolo[3,2,1-ij]quinolin-1-yl)-4-(1H-indol-3-yl)pyrrolidine-2,5-dione.

A feed solution for multicolumn chromatography (MCC) is prepared by dissolving Compound 8 DCM in methanol. The resulting DCM/methanol co-solvent is distilled until the residual level of DCM in the feed solution reaches a level acceptable for contact with the Chiral Stationary Phase (CSP), i.e., <0.1% by weight. The batch is diluted in a mixture of methanol/Acetonitrile (9:1) to a concentration of 50 mg/mL and introduced to the chromatographic system. Chiralpak AZ (CSP) can be utilized. The raffinate is monitored by chiral HPLC analysis and chromatographic parameters are tuned to obtain >99% chiral purity of (−)-trans-3-(5,6-dihydro-4H-pyrrolo[3,2,1-ij]quinolin-1-yl)-4-(1H-indol-3-yl)pyrrolidine-2,5-dione (Compound 10 in Scheme I). Raffinate is pooled and concentrated batchwise as the separation proceeds. The collected raffinate is taken to a larger reactor and the volume is reduced. Compound 10 is then isolated by crystallization.

Example 5

The present example describes batchwise generation of (−)-trans-3-(5,6-dihydro-4H-pyrrolo[3,2,1-ij]quinolin-1-yl)-4-(1H-indol-3-yl)pyrrolidine-2,5-dione from the undesired enantiomer, (+)-trans-3-(5,6-dihydro-4H-pyrrolo[3,2,1-ij]quinolin-1-yl)-4-(1H-indol-3-yl)pyrrolidine-2,5-dione.

In some instances, for instance when resolution is achieved using MCC, it is desirable to isolate and racemize the undesired enantiomer, (+)-trans-3-(5,6-dihydro-4H-pyrrolo[3,2,1-ij]quinolin-1-yl)-4-(1H-indol-3-yl)pyrrolidine-2,5-dione (Compound 9 in Scheme I), in a batchwise manner In one example of the process to generate crude Compound 8 from isolated Compound 9, the undesired enantiomer (6.46 kg) was charged to a 100-L reactor. Ethanol (60 L) was charged followed by the addition of solid NaOH (1.05 kg, 1.5 equiv). The resulting slurry was heated to 65° C. for 13 hours and then allowed to cool to ambient temperature over 4 hours. The mixture was sampled and analyzed by chiral HPLC showing a 54/46 ratio of enantiomers. The chemical purity was determined to be 94.6% (AUC) by HPLC. The slurry was then polish filtered through Celite, and the pad was rinsed with ethanol (13 L). The material that was removed was a brown film of solids with no large chunks. The solution was then recharged to the 100-L reactor and 2 M HCl (13.1 L, 1.5 equiv) was added over 35 minutes. During the addition, a thin slurry formed. The mixture was then stirred at ambient temperature (after 5 hours a thick light orange slurry was obtained). Water (25 L) was then added over 45 minutes, and the mixture was stirred for 2 hours. An aliquot was removed and filtered. The batch was then heated to 60° C. and stirred for 8 hours, and then allowed to slowly cool to improve the filtration properties of the solids. Crude Compound 8 [5.12 kg, 75.7% (accounts for 4.5 wt % ethanol)] was isolated with chemical purity of 99.39% (AUC) by HPLC. In this case the purity was sufficient to further process this material by MCC. The purity can be enhanced, if necessary, through formation of the DCM.

The chiral resolution of Compound 8 DCM to Compound 10 described in Example 4 and the recycling of Compound 9 to Compound 8 described in Example 5 are shown in Scheme IV.

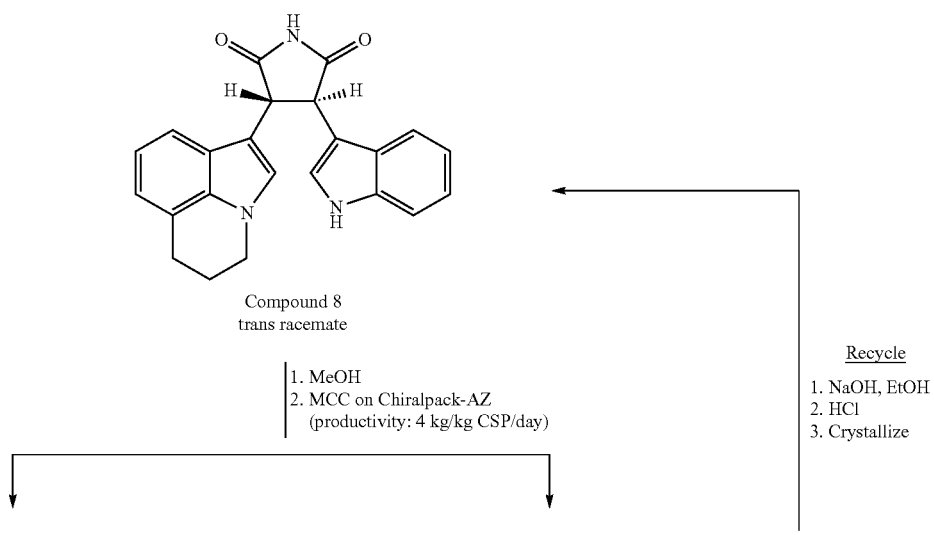

Scheme IV

Compound 8
trans racemate

1. MeOH
2. MCC on Chiralpack-AZ
   (productivity: 4 kg/kg CSP/day)

Recycle
1. NaOH, EtOH
2. HCl
3. Crystallize

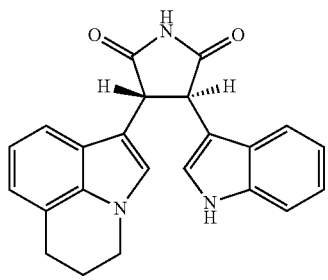

Compound 10
>99% (HPLC area)
>99% Chiral Purity (area %)

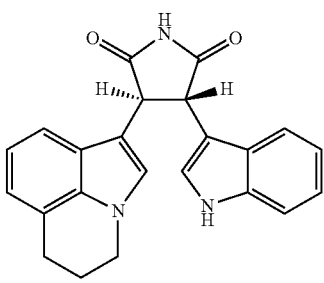

Compound 9
>99% (HPLC area)

Example 6

The present example describes the chiral resolution by diastereomeric salt formation and isolation of (−)-trans-3-(5,6-dihydro-4H-pyrrolo[3,2,1-ij]quinolin-1-yl)-4-(1H-indol-3-yl)pyrrolidine-2,5-dione.

As an alternative to chiral resolution by MCC, a resolution of the enantiomers, Compound 10 and Compound 9, can also be achieved by the preferential formation of a diastereomeric salt of Compound 10.

In one example, crude Compound 8 can be converted to (−)-trans-3-(5,6-dihydro-4H-pyrrolo[3,2,1-ij]quinolin-1-yl)-4-(1H-indol-3-yl)pyrrolidine-2,5-dione.(1S,2S)-(+)-pseudoephedrine (Compound 10.(1S,2S)-(+)-pseudoephedrine in Scheme I) using the following representative procedure. (1S,2S)-(+)-pseudoephedrine (601 g, 0.6 equiv) is dissolved in acetonitrile ($CH_3CN$) (11.2 L, 5 vol) at about 50° C. and stirred for approximately 30 minutes past dissolution. Crude Compound 8 [2.24 kg, 96.4% (AUC) by HPLC] is dissolved in $CH_3CN$ (11.2 L, 5 vol) at about 50° C. and then polish filtered through a pad of Celite. The Compound 8 solution is added via a drop tank to the (1S,2S)-(+)-pseudoephedrine solution over 20-30 minutes at about 50° C. Once the resulting solution begins to crystallize, shortly after completion of the Compound 8 addition, the mixture is stirred until it slowly cools to ambient temperature, then stirring is continued overnight (about 11 h total of cooling and stirring). The beige granular solids are filtered through an 18" stainless steel nutche filter and rinsed/re-slurried using $CH_3CN$ (7 L, 3.2 vol). The slurry is filtered, and the solids are slurried again with $CH_3CN$ (5 L, 2.3 vol). After drying on the nutche filter for 1 hour a sample is analyzed by HPLC. If the solids contain a higher than desired amount of the undesired diastereomeric salt, the solids can be re-slurried using $CH_3CN$ and dried before repeating the analysis. The solids are then dried under hot $N_2$ (51° C.) overnight. Typically, analysis of the Compound 10.(1S,2S)-(+)-pseudoephedrine shows an overall chemical purity of >99% (AUC) by HPLC and a chiral purity of >99% Compound 10. Using $^1$H NMR analysis, a typical sample is estimated to contain <0.5 wt % $CH_3CN$.

The Compound 10.(1S,2S)-(+)-pseudoephedrine can then be converted to Compound 10 by treatment with acid and crystallization from methanol or ethanol. A representative procedure is as follows: Compound 10.(1S,2S)-(+)-pseudoephedrine (50 g) is slurried in Methyltetrahydrofuran (MeTHF) (500 mL) and water (250 mL). 1 M HCl (110 mL) is added to the mixture to reach a final pH of 1.6. The resulting solution with a slight amount of solids is stirred for about one hour to dissolve the solids. The organic and aqueous layers are then separated. The organic layer is washed with a water/brine solution (1:1, 250 mL), separated, and 2-B ethanol (1000 mL) is added. The solution is then concentrated down to 200 mL and analyzed for MeTHF content (4.8 wt %). The solution is polish filtered, and Compound 10 seeds (0.2 g) are added (T=25° C.). The mixture is stirred for about three days with samples being taken periodically and analyzed for Compound 10 remaining in the mother liquor. The resulting slurry is filtered, and the solids are washed with 2-B ethanol (70 mL). The solids are dried for about three hours in a vacuum oven at about 60° C. to give Compound 10 [28.84 g, 82.7%, 99.60% (AUC) by HPLC, 0.54 wt % ethanol, 0.08 wt % MeTHF] as a beige solid.

The diasteromeric salt resolution of Compound 8 to Compound 10 described in Example 6 and the recycling of Compound 9 to Compound 8 described in Example 5 are shown in Scheme V.

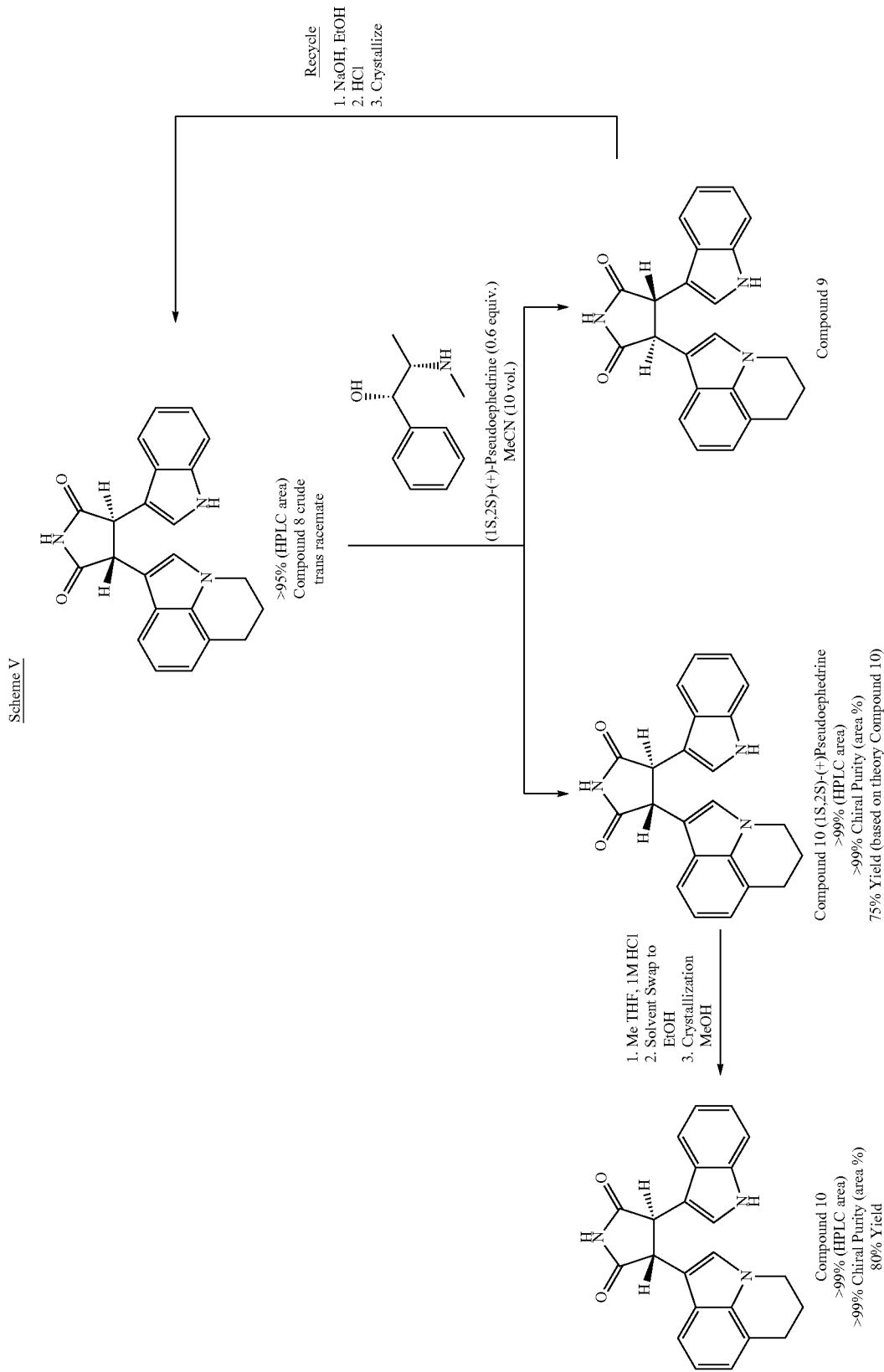

Example 7

The present example describes chiral separation by dynamic kinetic resolution (DKR).

As an alternative to chiral resolution by MCC or a traditional kinetic resolution by diastereomeric salt formation, a dynamic kinetic resolution (DKR) of the enantiomers Compound 10 and Compound 9 can also be achieved by the preferential formation of a diastereomeric salt of Compound 10 with simultaneous in situ racemization of Compound 9.

in a vacuum oven (50° C., 2 trays) for 18 hours. The solids were analyzed and showed Compound 10.(1S,2S)-(+)-pseudoephedrine [1.22 Kg, 74%, 99.3% (AUC) by HPLC, 99.2% (AUC) by chiral HPLC]. This process was carried out on 20 kg of Compound 8 to afford Compound 10.(1S,2S)-(+)-pseudoephedrine [18.9 kg, 70%, %, 98.8% (AUC) by HPLC, 99.1% (AUC) by chiral HPLC].

The dynamic kinetic resolution of Compound 8 to Compound 10 via Compound 10.(1S,2S)-(+)-pseudoephedrine is shown in Scheme VI.

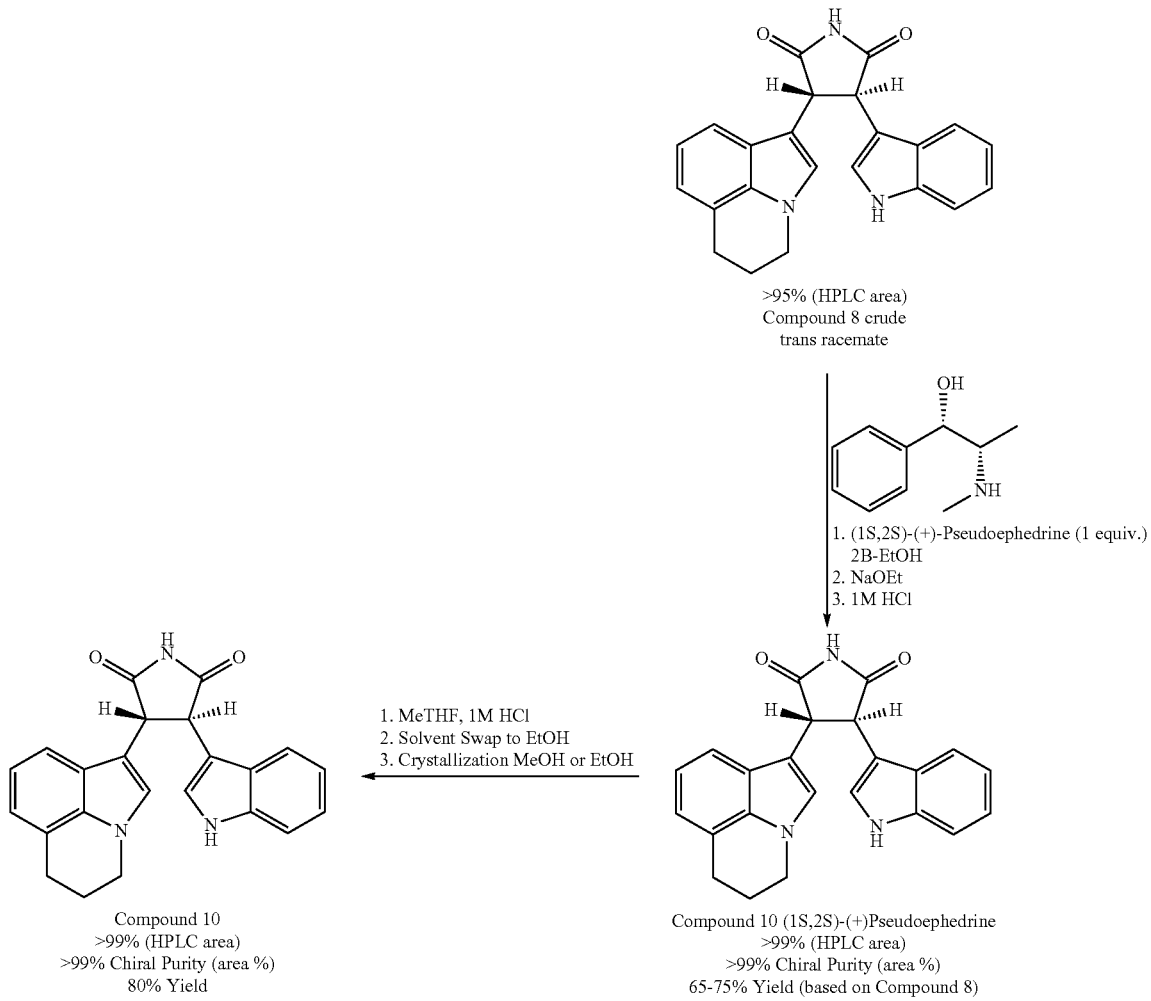

Scheme VI

In this process, crude Compound 8 can be converted to Compound 10.(1S,2S)-(+)-pseudoephedrine using the following representative procedure. Crude Compound 8 (1.25 kg, 96% AUC, 9.1 wt % solvent content) and (1S,2S)-(+)-pseudoephedrine (559 g, 1.0 equiv) were slurried in 2B-ethanol (11.25 L, 9 vol) and heated to 50° C. for 3 hours. The slurry was treated with 21 wt % NaOEt in methanol or ethanol (110 g, 0.1 equiv) and heated to 50° C. After 40 hours, the mixture was quenched by adding 1 M HCl (338 mL, 0.1 equiv) in water (786 mL, ~10% water relative to ethanol) over 5 minutes. The mixture was stirred at 50° C. for 1 hour, and then allowed to cool to ambient temperature over 0.5 hours. The slurry was stirred at room temperature for another 3 hours, and then filtered. The solids were washed with 10% water/2B-ethanol (3.75 L, 3 vol) and dried

Example 8

The present example describes chiral separation by dynamic kinetic resolution (DKR).

As an alternative to chiral resolution by MCC or a traditional kinetic resolution by diastereomeric salt formation, a dynamic kinetic resolution (DKR) of the enantiomers Compound 10 and Compound 9 can also be achieved by the preferential formation of a diastereomeric salt of Compound 10 with simultaneous in situ racemization of Compound 9.

In this process, crude Compound 8 (111.4 kg), Pd scavenger resin (PL-TMT-MP, 3.5 kg), and methanol (1507 L) were added to a container and heated to 45° C. for at least 16 hours. Upon completion of the reaction, the mixture was filtered to remove the Pd scavenger resin. The container was rinsed with methanol (104 L). The combined filtrate was distilled to ~600 L. (1S,2S)-(+)-pseudoephedrine (51.4 kg) and methanol (416 L) were added to the filtrate. The resulting solution was heated at 45° C. for 3-4 hours. Solids were precipitated and analyzed by HPLC to ensure the reaction was proceedingly selective. A solution of sodium methoxide in methanol (21% wt, 6.1 kg) was then added followed by methanol (11 L), and the resulting mixture was heated at 45° C. for an additional 18 hours. The reaction mixture was analyzed by HPLC for completion of the crystallization. Upon completion of the crystallization, the reaction mixture was treated with HCl solution (3.5 kg) to neutralize the base. The resulting mixture was cooled to ambient temperature and agitated for a minimum of 3 hours. The solids were then isolated by filtration, and the filter cake was washed with a solution of methanol and water (411 L to 46 L, respectively). The filter cake was colorless (if significant color persisted in the solids, the washing was repeated to remove the color). The solids were dried in a filter dryer at 55° C. under vacuum for a minimum of 8 hours and released for use in the next step as Compound 10.(1S,2S)-(+)-pseudoephedrine (101 kg).

Example 9

The present example describes a slurry method to prepare (−)-trans-3-(5,6-dihydro-4H-pyrrolo[3,2,1-ij]quinolin-1-yl)-4-(1H-indol-3-yl)pyrrolidine-2,5-dione.

Compound 10.(1S,2S)-(+)-pseudoephedrine (100.7 kg) and a solution of aqueous HCl (1M, 250 kg) and methanol (240 kg) were mixed, and the resulting slurry was heated to 50° C. and stirred for at least 2 hours. Upon completion of the reaction, the slurry was cooled to ambient temperature and stirred for a minimum of 1 hour. The solids were isolated by filtration, washed with a 50% solution of aqueous methanol (200 L), and dried under vacuum at 65° C. for at least 6 hours. The crude Compound 10 was dissolved in THF (96 kg) by heating the mixture to 50° C. The resulting solution was polish filtered, followed by the addition of methanol (200 kg). The solution was then concentrated azeotropically and atmospherically by distillation to reduce the THF content. Once the volume of the solution was reduced to 250 L, additional methanol (200 L) was added, and the concentration process was repeated. This process was repeated until the THF content was reduced to less than 5% (vol./vol.). During the addition of methanol, one or more crystals of Compound 10 (300 g) were also introduced in order to facilitate crystallization. The crystals were isolated by filtration, washed with additional 50% aqueous methanol, and dried under vacuum at 65° C. for at least 12 hours. Crude Compound 10 (60.6 kg) was isolated as a red-brown solid.

Example 10

The present example describes a slurry method to prepare Form 1 polymorph of (−)-trans-3-(5,6-dihydro-4H-pyrrolo[3,2,1-ij]quinolin-1-yl)-4-(1H-indol-3-yl)pyrrolidine-2,5-dione.

Crude Compound 10 was prepared as described in Example 9. The crude Compound 10 was dissolved in THF (96 kg) by heating the mixture to 50° C. The resulting solution was polish filtered, followed by the addition of methanol (200 kg) and Form 1 of Compound 10 as seeds to impart polymorphic control of the crystallization process. Seeds to impart polymorphic control were taken from representative batches in which characterization data had confirmed that the crystalline material was of the desired polymorphic form. The solution was then concentrated azeotropically and atmospherically by distillation to reduce the THF content. Once the volume of the solution was reduced to 250 L, additional methanol (200 L) was added, and the concentration process was repeated. This process was repeated until the THF content was reduced to less than 5% (vol./vol.). The temperature of the solution was then reduced to 50° C. and stirred for at least 4 hours. Aliquots were removed to confirm formation of the desired polymorph. If required, the polymorph can be redissolved in THF (30% of batch volume), polish filtered, concentrated and seeded to obtain the desired polymorph. When the desired polymorph was obtained, a solution of 50% aqueous methanol was added at 50° C., and the solution was agitated for an additional 2-3 hours. The solution was then cooled to ambient temperature and held for at least 2 hours to allow crystallization. Upon completion, the crystals were isolated by filtration, washed with additional 50% aqueous methanol, and dried under vacuum at 65° C. for at least 12 hours. Polymorphic Form 1 of Compound 10 (60.6 kg) was isolated as a red-brown solid.

Form 2 polymorph of (−)-trans-3-(5,6-dihydro-4H-pyrrolo[3,2,1-ij]quinolin-1-yl)-4-(1H-indol-3-yl)pyrrolidine-2,5-dione can also be prepared with the above method if the Form 1 seed crystal is replaced by the Form 2 seed crystal.

Example 11

Example 11 describes a method to generate XRPD diffractograms of polymorphs of (−)-trans-3-(5,6-dihydro-4H-pyrrolo[3,2,1-ij]quinolin-1-yl)-4-(1H-indol-3-yl)pyrrolidine-2,5-dione X-Ray Powder Diffraction patterns were collected on a Siemens D5000 diffractometer using Cu K$\alpha$ radiation (40 kV, 40 mA), $\theta$-$\theta$ goniometer, divergence of V20 and receiving slits, a graphite secondary monochromator and a scintillation counter. The instrument performance is checked using a certified Corundum standard (NIST 1976). The software used for data collection was Diffrac Plus XRD Commander v2.3.1 and the data were analyzed and presented using Diffrac Plus EVA v 11,0.0.2 or v 13.0.0.2.

Powder samples were prepared as flat plate specimens. Approximately 35 mg of the sample was gently packed into a cavity cut into polished, zero-background (510) silicon wafer. The sample was rotated in its own plane during analysis. The details of the data collection are:

Angular range: 2 to 42° $\theta$
Step size: 0.05° 2$\theta$
Collection time: 4 s/step.

Example 12

Example 12 describes a method to generate XRPD diffractograms of polymorphs of (−)-trans-3-(5,6-dihydro-4H-pyrrolo[3,2,1-ij]quinolin-1-yl)-4-(1H-indol-3-yl)pyrrolidine-2,5-dione High resolution X-Ray Powder Diffraction patterns were collected on a Bruker D8 diffractometer using Cu K$\alpha$ radiation (40 kV, 40 mA), $\theta$-2$\theta$ goniometer, and a divergence of V4 and receiving slits, a Ge-monochromator and a Lynxeye detector. The instrument performance is checked using a certified Corundum standard (NIST 1976). The software used for data collection was Diffrac Plus XRD Commander v2.5.0 and the data were analyzed and presented using Diffrac Plus EVA v 11,0.0.2 or v 13.0.0.2.

Samples were run under ambient conditions as flat plate specimens using powder as received. Approximately 100 mg of the sample was gently packed into a circular cavity cut into polished, zero-background (510) silicon wafer. The sample was rotated in its own plane during analysis. The details of the data collection for the generic procedure are:
Angular range: 2 to 42° 2θ
Step size: 0.05° 2θ
Collection time: 5 s·step$^{-1}$

Example 13

Example 13 describes XRPD patterns from polymorphs of (−)-trans-3-(5,6-dihydro-4H-pyrrolo[3,2,1-ij]quinolin-1-yl)-4-(1H-indol-3-yl)pyrrolidine-2,5-dione Two non-solvated polymorphs of (−)-trans-3-(5,6-dihydro-4H-pyrrolo[3,2,1-ij]quinolin-1-yl)-4-(1H-indol-3-yl)pyrrolidine-2,5-dione: Form 1 and Form 2 (See, FIGS. 12A, 12B, 13A and 13B).

Form 1 shows a XRPD pattern comprising 2θ values in degrees of 8.2, 10.8 and 14.1. (See, FIGS. 12A and 12B, and Table 1)

Form 2 shows a XRPD patter comprising 2θ values in degrees of 6.5, 9.9 and 12.0. (See, FIG. 13A and FIG. 13B, and Table 1)

TABLE 1

| Form 1 | 8.2 area | 10.8 area | 14.1 area | Total area | Form 2 | 6.5 area | 9.9 area | 12.0 area | Total area |
|---|---|---|---|---|---|---|---|---|---|
| 1 | 3.925 | 14.08 | 6.646 | 24.651 | 1 | 6.433 | 5.284 | 10.40 | 22.117 |
| 2 | 3.866 | 13.98 | 6.608 | 24.454 | 2 | 6.437 | 5.365 | 10.51 | 22.312 |
| 3 | 3.847 | 14.03 | 6.625 | 24.502 | 3 | 6.504 | 5.341 | 10.49 | 22.335 |
| 4 | 3.880 | 13.99 | 6.556 | 24.426 | 4 | 6.467 | 5.321 | 10.44 | 22.228 |
| 5 | 3.889 | 13.88 | 6.619 | 24.388 | 5 | 6.484 | 5.331 | 10.50 | 22.315 |
| 6 | 3.854 | 13.92 | 6.586 | 24.360 | 6 | 6.502 | 5.281 | 10.38 | 22.163 |
| mean | 3.88 | 14.0 | 6.61 | 24.464 | mean | 6.47 | 5.32 | 10.45 | 22.245 |
| RSD (%) | 0.73 | 0.52 | 0.48 | 0.43 | RSD (%) | 0.00 | 0.00 | 0.01 | 0.02 |

Example 14

Figure 16:
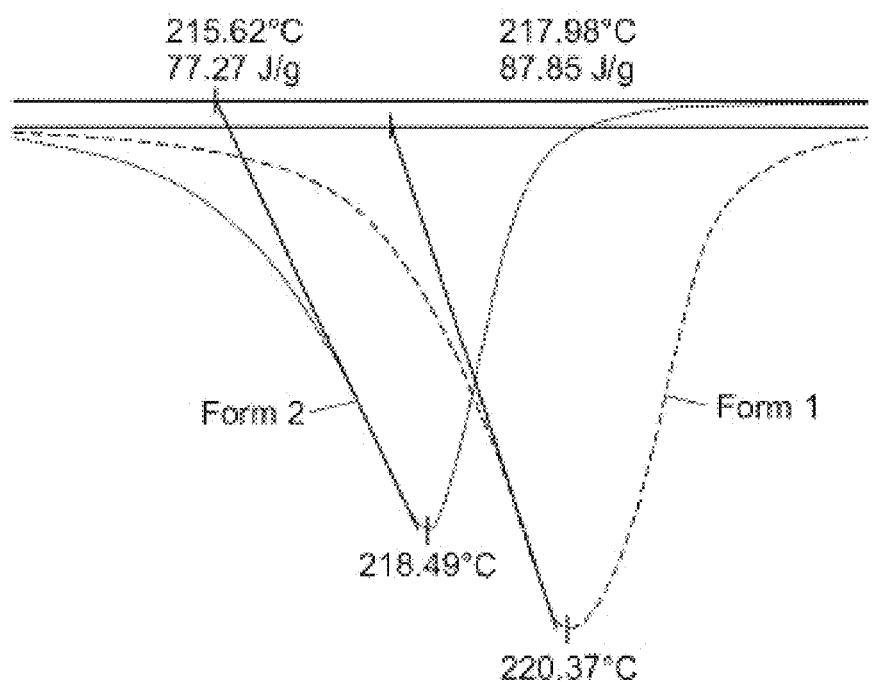
FIG. 16 sets forth graphics showing the thermal (melting) behavior of (−)-trans-3-(5,6-dihydro-4H-pyrrolo[3,2,1-ij]quinolin-1-yl)-4-(1H-indol-3-yl)pyrrolidine-2,5-dione Forms 1 and 2.

Form 1 is more thermodynamically stable than Form 2 as determined in interconversion experiments. Form 1 is orthorhombic and contains four molecules of (−)-trans-3-(5,6-dihydro-4H-pyrrolo[3,2,1-ij]quinolin-1-yl)-4-(1H-indol-3-yl)pyrrolidine-2,5-dione per cell. Form 1 has a melting point of ~218° C. recorded in DSC (See, FIG. 16).

Form 2 is comprised of birefringent rod-like crystals. No discernible change in crystalline form or purity was observed upon storage of multiple batches of Form 2 at 40° C./75% RH for up to six months and 25° C./60% RH for up to 12 months. The space group of Form 2 was either $P2_1$ or P2: there are two molecules of (−)-trans-3-(5,6-dihydro-4H-pyrrolo[3,2,1-ij]quinolin-1-yl)-4-(1H-indol-3-yl)pyrrolidine-2,5-dione in the unit cell (one molecule in the asymmetric unit), and there is no excess volume in the unit cell that is occupied by a solvent molecule. Form 2 has a melting point of ~216° C. recorded in DSC (See, FIG. 16).

Figure 14:
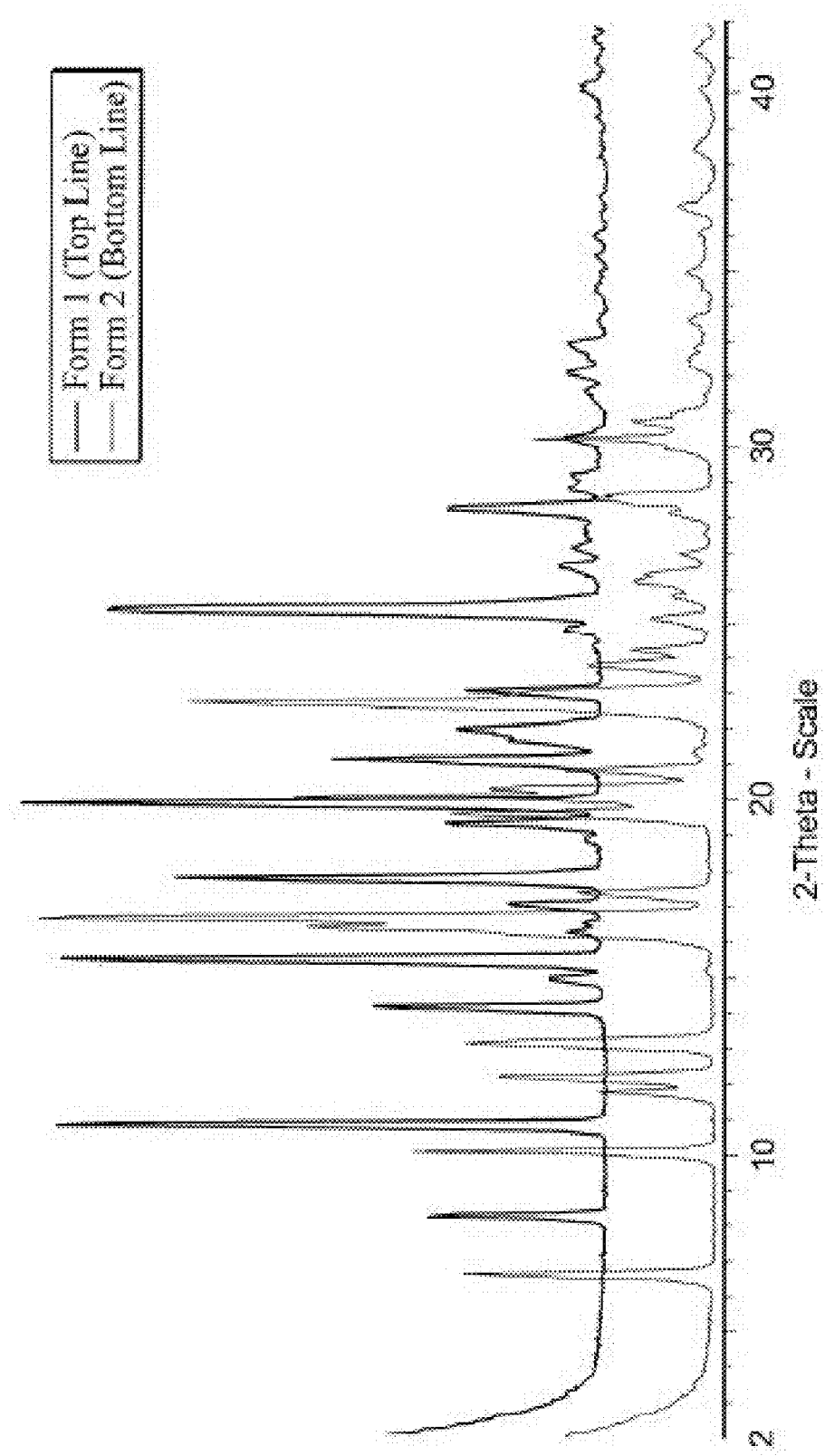
FIG. 14 sets forth graphics comparing the XRPD patterns of Forms 1 and 2 polymorphs of (−)-trans-3-(5,6-dihydro-4H-pyrrolo[3,2,1-ij]quinolin-1-yl)-4-(1H-indol-3-yl)pyrrolidine-2,5-dione.
Figure 15A:
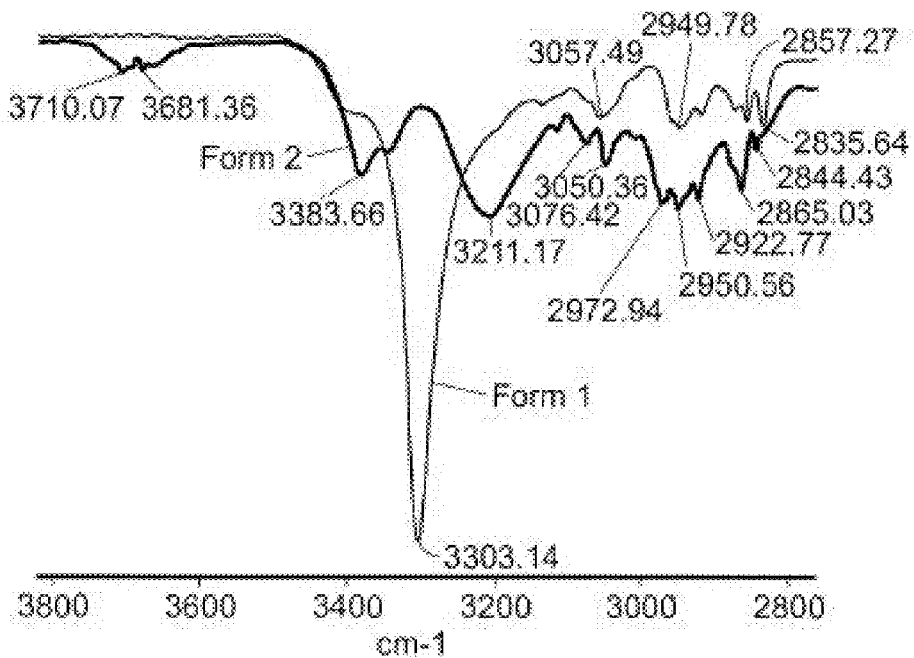
FIGS. 15A and 15B set forth graphics showing the IR spectra of Forms 1 and 2 of (−)-trans-3-(5,6-dihydro-4H-pyrrolo[3,2,1-ij]quinolin-1-yl)-4-(1H-indol-3-yl)pyrrolidine-2,5-dione.
Figure 15B:
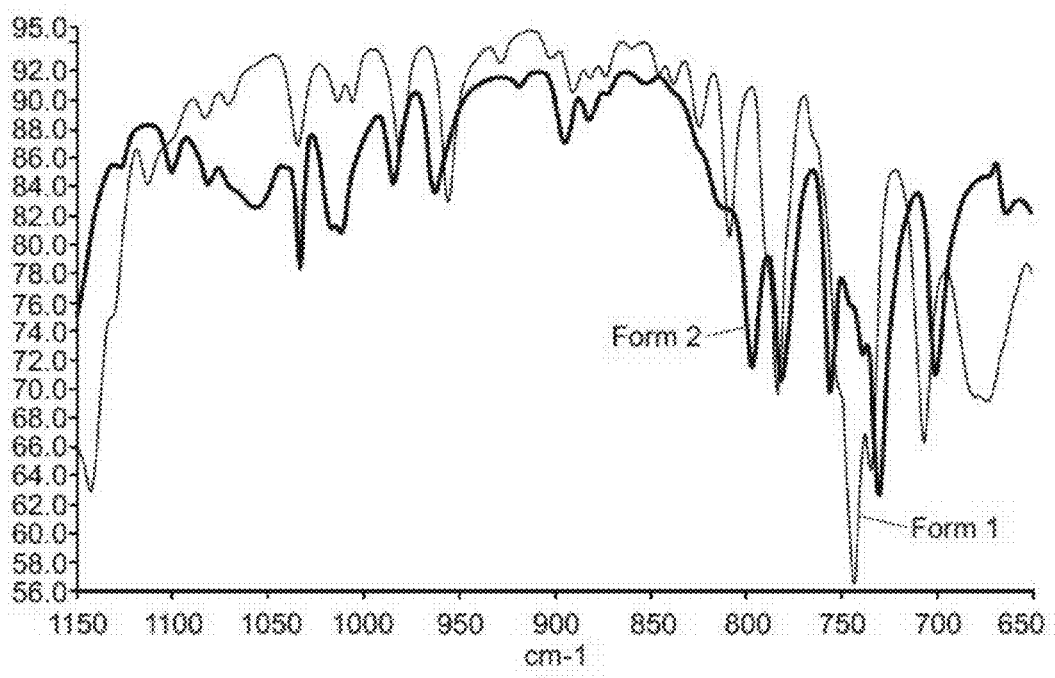

Upon scale-up of the Compound 10 process to >5 kg production as a single batch, Form 1 was spontaneously produced Infra-red (IR) and X-ray powder diffraction (XRPD) were determined to be effective analytical tools for the identification and differentiation of the two forms (See, FIGS. 14, 15A and 15B). The process was readily controlled via seeding demonstrated at a 7-kg scale.

The two polymorphs can be interconverted when proper conditions are used to control the crystallization process. Form 2 can be obtained by dissolving Form 1 in methanol, seeding with Form 2 and evaporating the mixture to dryness by rotary evaporation. The successful conversion was determined to be Form 2 by IR analysis and corroborated by XRPD analysis.

Example 15

The IR spectrum of Form 1 displayed an intense vibration centered at ~3300 cm$^{-1}$ that was not observed in Form 2 (FIG. 15A), whereas the IR spectrum of Form 2 showed a relatively intense peak centered at ~800 cm$^{-1}$ which was not observed in Form 1 (FIG. 15B).

Figure 17A:
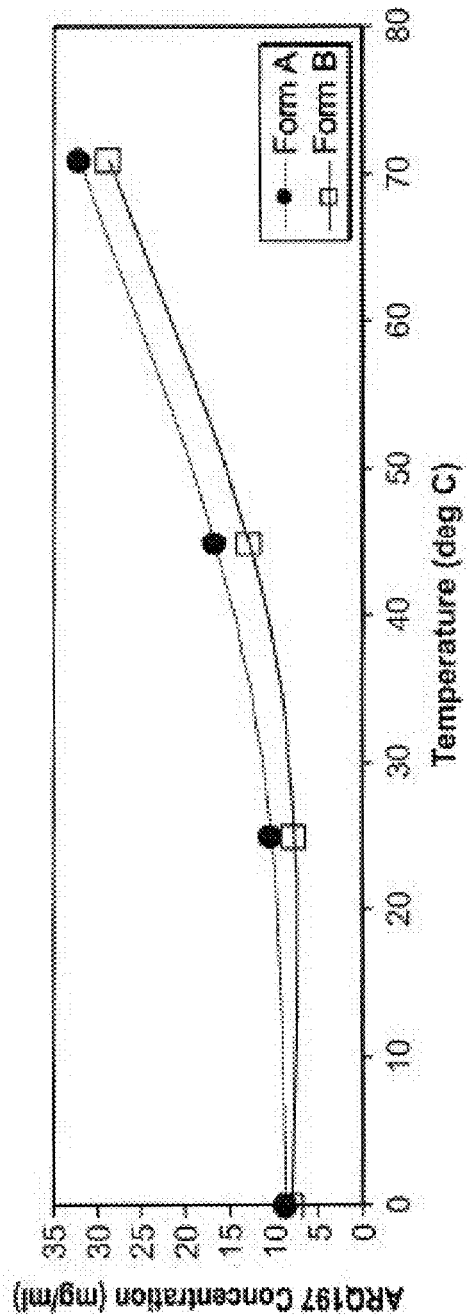
FIGS. 17A and 17B set forth graphics showing the solubility and intrinsic dissolution of (−)-trans-3-(5,6-dihydro-4H-pyrrolo[3,2,1-ij]quinolin-1-yl)-4-(1H-indol-3-yl)pyrrolidine-2,5-dione Forms 1 and 2, depicted as Forms B and A, respectively.
Figure 17B:
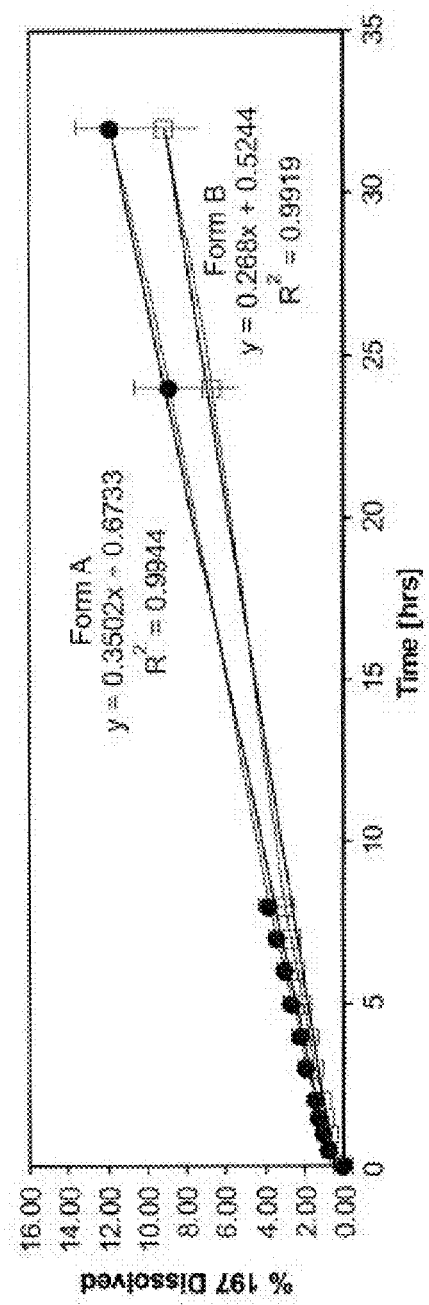

Form 1 and Form 2 have different equilibrium solubilities: Form 2=0.61 mg/mL and Form 1=0.51 mg/mL. FIG. 17A shows the solubility of Forms 1 and 2 in methanol from 0-70° C. FIG. 17B shows the intrinsic solubility of Forms 1 and 2 in 50 mM pH 6.8 phosphate buffer/1% SLS.

Example 16

Exponentially growing MDA-MB-231 cells or MIA PaCa-2 (also known as PACA-2) cells were seeded at 1,000 cells per well in six-well plates and allowed to attach for 24 hours. MDA-MB-231 and MIA PaCa-2 cells were cultured in DMEM supplemented with 10% (v/v) fetal bovine serum (FBS) and 5 ml Penicillin/Streptomycin at 37° C. in 5% $CO_2$. MDA-MB-231 and MIA PaCa-2 were established in estrogen receptor-negative human breast cancer and pancreatic carcinoma cell lines, respectively. (±)-cis-3-(5,6-dihydro-4H-pyrrolo[3,2,1-ij]quinolin-1-yl)-4-(1H-indol-3-yl)pyrrolidine-2,5-dione or (±)-trans-3-(5,6-dihydro-4H-pyrrolo[3,2,1-ij]quinolin-1-yl)-4-(1H-indol-3-yl)pyrrolidine-2,5-dione were each dissolved at a concentration of 10 mM in DMSO, and separately added to cells at a concentration of 0.1, 0.25, 0.5, 1 or 2 µM. Control plates received DMSO alone, at the same percentage of total culture volume as that administered in conjunction with the highest concentration of drug. Cell cultures were observed daily for 10-15 days, then fixed and stained with modified Wright-Giemsa stain (Sigma). Treatment with (±)-cis-3-(5,6-dihydro-4H-pyrrolo[3,2,1-ij]quinolin-1-yl)-4-(1H-indol-3-yl)pyrrolidine-2,5-dione or (±)-trans-3-(5,6-dihydro-4H-pyrrolo[3,2,1-ij]quinolin-1-yl)-4-(1H-indol-3-yl)pyrrolidine-2,5-dione results in cell death of MDA-MB-231 cells or Paca-2 cells. See, e.g., FIGS. 2A, 2B, 2C, and 2D. The $IC_{50}$ for (±)-cis-3-(5,6-dihydro-4H-pyrrolo[3,2,1-ij]quinolin-1-yl)-4-(1H-indol-3-yl)pyrrolidine-2,5-dione was found to be 0.5 µM. The $IC_{50}$ value for (±)-trans-3-(5,6-dihydro-4H-pyrrolo[3,2,1-ij]quinolin-1-yl)-4-(1H-indol-3-yl)pyrrolidine-2,5-dione was found to be 0.5 µM.

Example 17

Figure 3A:
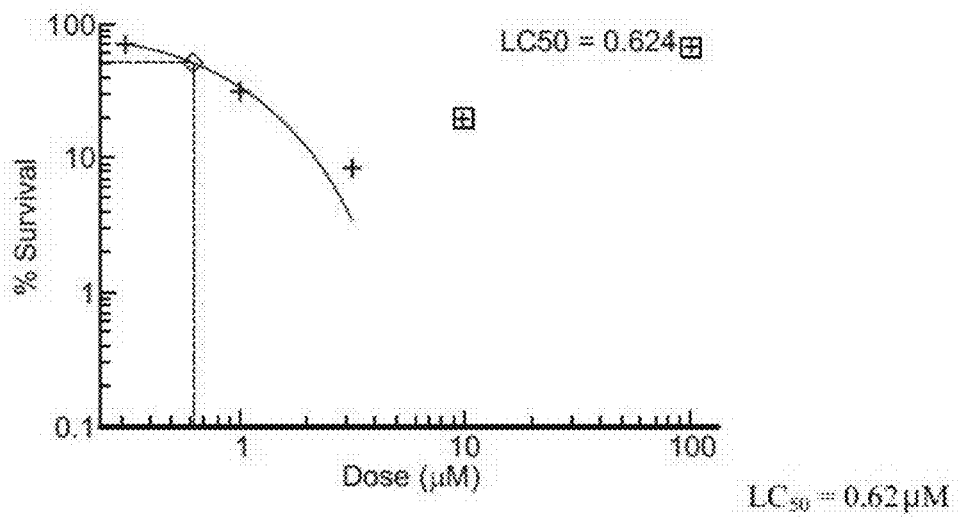
FIGS. 3A and 3B set forth an effect of (−)-trans-3-(5,6-dihydro-4H-pyrrolo[3,2,1-ij]quinolin-1-yl)-4-(1H-indol-3-yl)pyrrolidine-2,5-dione (FIG. 3A) or (+)-trans-3-(5,6-dihydro-4H-pyrrolo[3,2,1-ij]quinolin-1-yl)-4-(1H-indol-3-yl)pyrrolidine-2,5-dione (FIG. 3B) on survival of MDA-MB-231 cells in vitro.
Figure 3B:
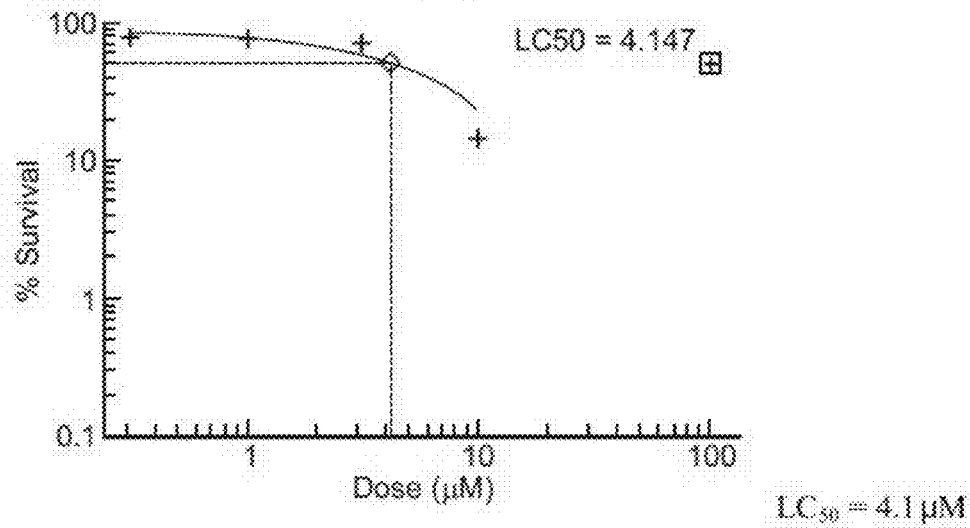

MDA-MB-231 cells (ATCC #HTB-26), grown in DMEM plus 15% heat inactivated fetal bovine serum plus 10 mM HEPES pH 7.5, were plated in 60 mm$^2$ plates (2×10$^5$ cells per plate). After two days candidate compounds in DMSO at various concentrations were diluted in media and added to individual plates such that the final DMSO concentration in the cell culture media was 0.1%. After two days incubation the culture was trypsinized, cells were washed with media, counted using a hemocytometer and 500 cells, including cell bodies, were plated in 100 mm² plates in media. Two weeks later the media was removed and the cell colonies were fixed with methanol for 10 minutes, stained with 1% crystal violet for 10 minutes, washed with water and air dried. Cell colonies were visually counted when there were greater then 50 cells present per colony. Plating efficiency was defined as the average number of colonies formed divided by 500. The surviving fraction was defined as the plating efficiency of a candidate compound divided by the plating efficiency of DMSO multiplied by 100. For candidate compound titrations, the $IC_{50}$ value was determined by fitting the equation $y=Ae^{Bx}$ to the data points and extrapolating the concentration where surviving fraction equaled 50. Treatment with (−)-trans-3-(5,6-dihydro-4H-pyrrolo[3,2,1-ij]quinolin-1-yl)-4-(1H-indol-3-yl)pyrrolidine-2,5-dione or (+)-trans-3-(5,6-dihydro-4H-pyrrolo[3,2,1-ij]quinolin-1-yl)-4-(1H-indol-3-yl)pyrrolidine-2,5-dione results in cell death of MDA-MB-231 cells. See, e.g., FIGS. 3A and 3B. The $IC_{50}$ for (−)-trans-3-(5,6-dihydro-4H-pyrrolo[3,2,1-ij]quinolin-1-yl)-4-(1H-indol-3-yl)pyrrolidine-2,5-dione was found to be 0.62 µM. The $IC_{50}$ for (+)-trans-3-(5,6-dihydro-4H-pyrrolo[3,2,1-ij]quinolin-1-yl)-4-(1H-indol-3-yl)pyrrolidine-2,5-dione was found to be 4.1 µM.

Example 18

Recombinant Protein Kinase C (Calbiochem) (100 ng) was incubated with (±)-cis-3-(5,6-dihydro-4H-pyrrolo[3,2,1-ij]quinolin-1-yl)-4-(1H-indol-3-yl)pyrrolidine-2,5-dione or (±)-trans-3-(5,6-dihydro-4H-pyrrolo[3,2,1-ij]quinolin-1-yl)-4-(1H-indol-3-yl)pyrrolidine-2,5-dione at 0.05, 0.5, or 10 µM for 15 minutes at room temperature. Subsequently, a radioactive labeling mix in kinase buffer (20 mM Tris-HCl pH 7.5, 10 mM $MgCl_2$) containing 20 µM ATP, 0.2 µCi/µl $\delta^{32}$P-ATP, 0.2 µg/µl Histone H1 (Upstate Biotechnology/Millipore, Bedford, Mass.) was added to each sample. The kinase reaction was carried out for 5 minutes at room temperature. Reaction products were analyzed by 12% SDS-PAGE and autoradiography.

Figure 4:
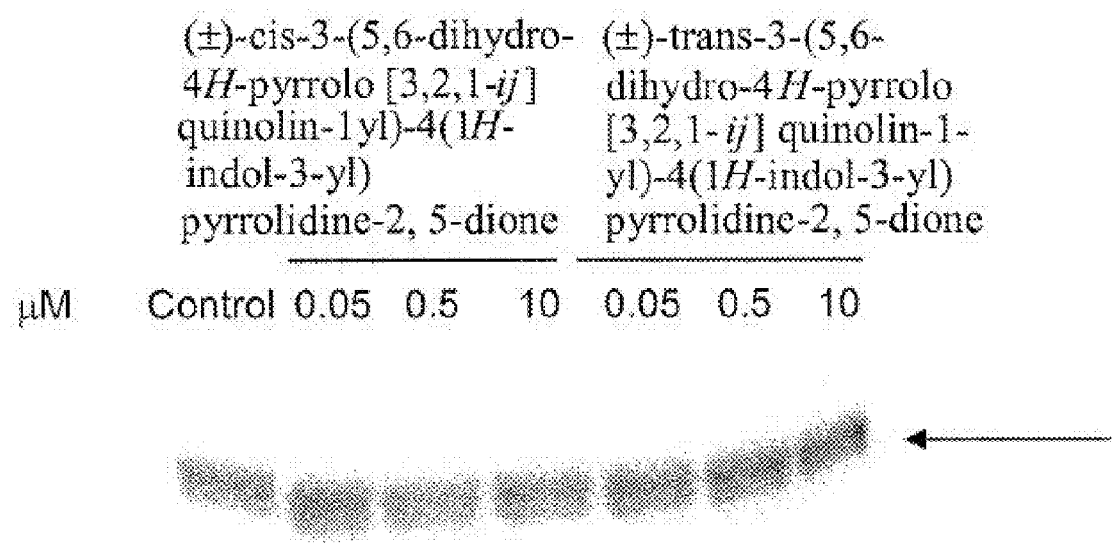
FIG. 4 sets forth an effect of (±)-cis-3-(5,6-dihydro-4H-pyrrolo[3,2,1-ij]quinolin-1-yl)-4-(1H-indol-3-yl)pyrrolidine-2,5-dione or (±)-trans-3-(5,6-dihydro-4H-pyrrolo[3,2,1-ij]quinolin-1-yl)-4-(1H-indol-3-yl)pyrrolidine-2,5-dione on Protein Kinase C activity in vitro.

Treatment of recombinant Protein Kinase C for 15 minutes at room temperature with (±)-cis-3-(5,6-dihydro-4H-pyrrolo[3,2,1-ij]quinolin-1-yl)-4-(1H-indol-3-yl)pyrrolidine-2,5-dione or (±)-trans-3-(5,6-dihydro-4H-pyrrolo[3,2,1-ij]quinolin-1-yl)-4-(1H-indol-3-yl)pyrrolidine-2,5-dione at the tested concentrations did not reduce kinase activity in comparison to treatment with carrier alone. See, e.g., FIG. 4.

Example 19

Figure 5A:
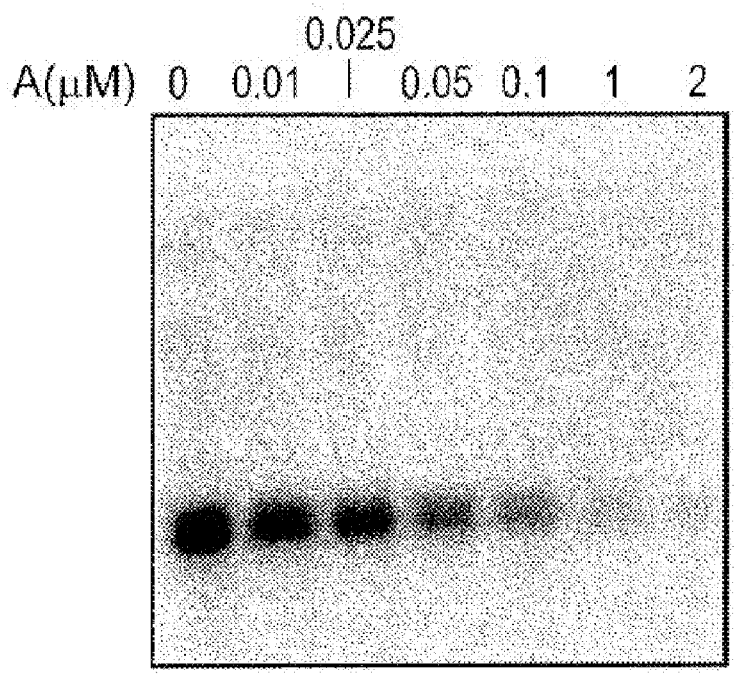
FIGS. 5A and 5B set forth inhibition of autophosphorylation of c-Met by (−)-trans-3-(5,6-dihydro-4H-pyrrolo[3,2,1-ij]quinolin-1-yl)-4-(1H-indol-3-yl)pyrrolidine-2,5-dione (FIG. 5A), and inhibition of induced c-Met phosphorylation by (−)-trans-3-(5,6-dihydro-4H-pyrrolo[3,2,1-ij]quinolin-1-yl)-4-(1H-indol-3-yl)pyrrolidine-2,5-dione or (+)-trans-3-(5,6-dihydro-4H-pyrrolo[3,2,1-ij]quinolin-1-yl)-4-(1H-indol-3-yl)pyrrolidine-2,5-dione (FIG. 5B).
Figure 5B:
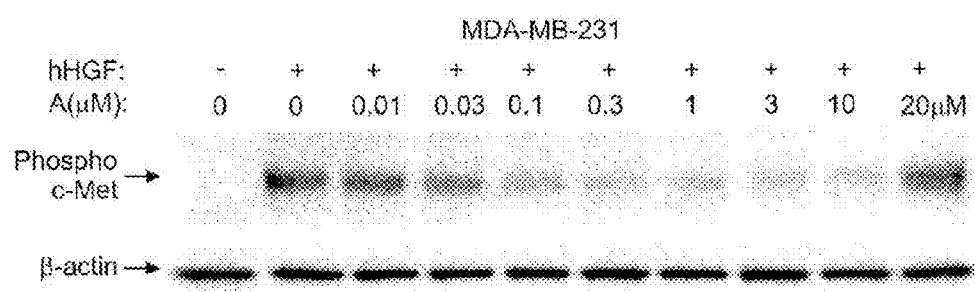

MDA-MB-231 cells were serum-deprived overnight (16 hours) in the absence or in the presence of the indicated concentrations of the separate enantiomers (+)-trans-3-(5,6-dihydro-4H-pyrrolo[3,2,1-ij]quinolin-1-yl)-4-(1H-indol-3-yl)pyrrolidine-2,5-dione and (−)-trans-3-(5,6-dihydro-4H-pyrrolo[3,2,1-ij]quinolin-1-yl)-4-(1H-indol-3-yl)pyrrolidine-2,5-dione. Cells were treated with 100 ng/ml recombinant human Hepatocyte Growth Factor/Scatter Factor (HGF/SF) (R&D Systems #294-HG) for 10 minutes. Whole cell extracts were prepared in lysis buffer (20 mM Tris-HCl pH 7.5, 150 mM NaCl, 1 mM $Na_2EDTA$, 1 mM EGTA, 1% Triton X-100, 2.5 mM sodium pyrophosphate, 1 mM beta-glycerophosphate, 1 mM $Na_3VO_4$, 1 µg/ml leupeptin, 1 mM phenylmethylsulfonyl fluoride) and sonicated. Protein concentration was measured by Bradford assay using the BioRad reagent (BioRad, Hercules, Calif.), according to the manufacturer's directions. Samples (50 µg of protein) were resolved by 8% SDS-PAGE under reducing conditions and transferred onto a PVDF membrane (Bio-Rad). The membrane was incubated 1 hour in TBS-T (50 mM Tris-HCl (pH=7.6), 200 mM NaCl, 0.05% Tween 20) with 5% milk. Proteins were detected by incubation overnight at 4° C. in TBS-T with 5% milk and either a polyclonal antibody against phosphorylated c-Met (#3121) or a monoclonal antibody against β-actin (A-5441) (Sigma), which was used as a control for total protein loading. After extensive washing in TBS-T, a horseradish peroxidase-conjugated anti-rabbit IgG (1:5000) or anti-mouse IgG (1:2000) (Amersham Biosciences) was added for 1 hour, and specific protein bands were visualized using an enhanced chemiluminescence detection system (Amersham Biosciences), according to the manufacturer's instructions. See, e.g., FIGS. 5A and 5B.

Treatment with (−)-trans-3-(5,6-dihydro-4H-pyrrolo[3,2,1-ij]quinolin-1-yl)-4-(1H-indol-3-yl)pyrrolidine-2,5-dione inhibits both basal and HGF-induced autophosphorylation of c-Met at a concentration of at least 30 nM. In contrast, (+)-trans-3-(5,6-dihydro-4H-pyrrolo[3,2,1-ij]quinolin-1-yl)-4-(1H-indol-3-yl)pyrrolidine-2,5-dione had only a minimum inhibitory effect on c-Met phosphorylation at much greater concentrations (20 µM). See, e.g., FIGS. 5A and 5B.

Example 20

A549 human lung cancer cells in a 96-well plate (Costar 3603, 5,000/well) were treated with either A) DMSO as a control; B) 1.2 µM (−)-trans-3-(5,6-dihydro-4H-pyrrolo[3,2,1-ij]quinolin-1-yl)-4-(1H-indol-3-yl)pyrrolidine-2,5-dione for 38 hours before addition of 1:200 fluorescent Annexin V (green) and 1:500 Propidium iodide (magenta, final concentration of 1 µg/mL). The labeling procedure was allowed to process at 37° C. for 20 minutes followed by image acquisition and analysis using an IC100 Image Cytometer (Beckman Coulter, Inc) with 10× amplification.

Figures 6A, 6B:
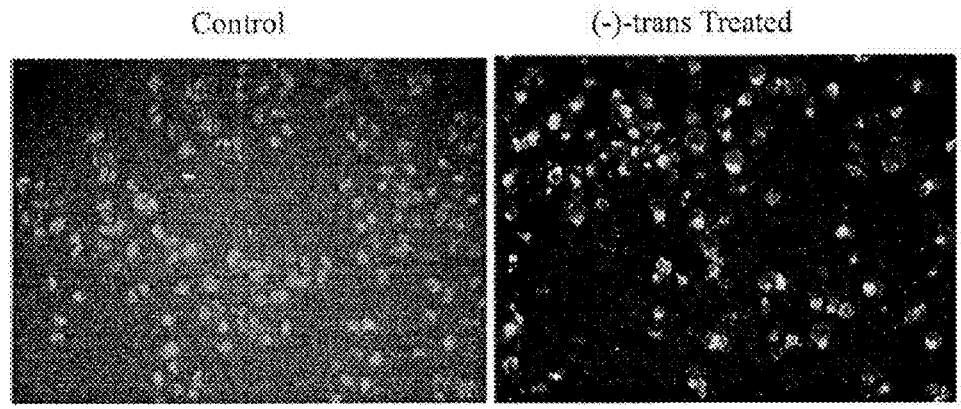
FIGS. 6A and 6B set forth an effect of (−)-trans-3-(5,6-dihydro-4H-pyrrolo[3,2,1-ij]quinolin-1-yl)-4-(1H-indol-3-yl)pyrrolidine-2,5-dione to induce apoptosis in cancer cells.

To determine whether (−)-trans-3-(5,6-dihydro-4H-pyrrolo[3,2,1-ij]quinolin-1-yl)-4-(1H-indol-3-yl)pyrrolidine-2,5-dione works primarily through a cytostatic or apoptotic mechanism, cancer cells exposed to (−)-trans-3-(5,6-dihydro-4H-pyrrolo[3,2,1-ij]quinolin-1-yl)-4-(1H-indol-3-yl)pyrrolidine-2,5-dione were stained with fluorescently labeled Annexin V (green fluorescence) and propidium iodide (bright magenta fluorescence). Annexin V is a well-validated reagent that specifically binds with high affinity to externalized membrane phosphatidylserine, an early marker of the onset of apoptosis, while propidium iodide is a marker for dead cells. Incubation of human lung cancer cells (A549) with 1.2 µM (−)-trans-3-(5,6-dihydro-4H-pyrrolo[3,2,1-ij]quinolin-1-yl)-4-(1H-indol-3-yl)pyrrolidine-2,5-dione for 38 hours induced cells to undergo apoptosis as evidenced by strong Annexin V staining. A small percentage of cells (~10-20%) co-stain with both Annexin V and propidium iodide, indicating that a sub-population of (−)-trans-3-(5,6-dihydro-4H-pyrrolo[3,2,1-ij]quinolin-1-yl)-4-(1H-indol-3-yl)pyrrolidine-2,5-dione treated cells were already dead within 38 hours. These data are consistent with (−)-trans-3-(5,6-dihydro-4H-pyrrolo[3,2,1-ij]quinolin-1-yl)-4-(1H-indol-3-yl)pyrrolidine-2,5-dione inducing cell death largely through activation of apoptotic mechanisms. (See, FIGS. 6A and 6B)

Example 21

MDA-MB-231 cells were pretreated with indicated concentrations of (−)-trans-3-(5,6-dihydro-4H-pyrrolo[3,2,1-ij]quinolin-1-yl)-4-(1H-indol-3-yl)pyrrolidine-2,5-dione for 24 hours. 300 µl of each cell suspension (at a concentration 0.5×10⁶ cells/mL in serum free medium) was placed in individual inserts and incubated for 24 hours at 37° C. The bottom wells housing the inserts contained 500 µl of 10%

Figure 7:
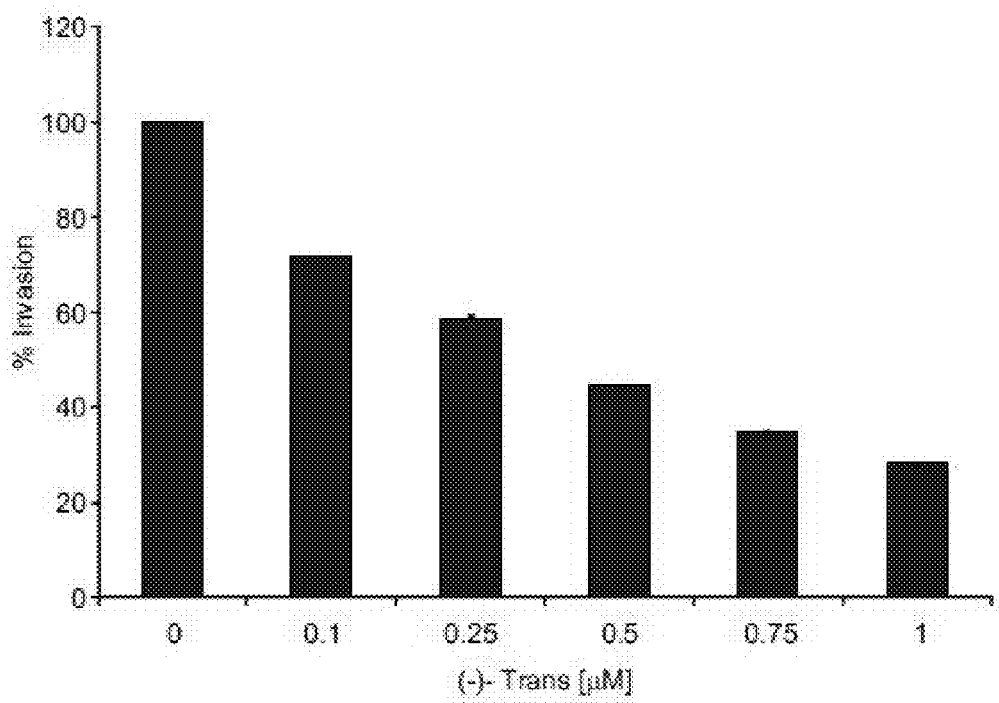
FIG. 7 sets forth an effect of (−)-trans-3-(5,6-dihydro-4H-pyrrolo[3,2,1-ij]quinolin-1-yl)-4-(1H-indol-3-yl)pyrrolidine-2,5-dione to inhibit metastatic cancer cell invasion.

FBS containing medium. At 24 hours the medium from each insert was aspirated, and cells that failed to invade were gently removed from the interior of the inserts with a cotton tipped swab. Each insert was then transferred to a clean well containing cell stain solution and incubated for 10 minutes at room temperature. The bottom of the insert was destained by incubating in extraction solution and OD was measured at 560 nM. (−)-trans-3-(5,6-dihydro-4H-pyrrolo[3,2,1-ij]quinolin-1-yl)-4-(1H-indol-3-yl)pyrrolidine-2,5-dione inhibited the migration across interstices in confluent cultures of MDA-MB-231 cancer cells. The data represent the mean of two independent experiments. (See FIG. 7)

The morbidity and mortality resulting from most cancers is the result of local invasion and metastasis from the primary tumors to other tissues. This process mostly depends on the motility and growth of tumor cells. Activation of c-Met by HGF induces a variety of cellular responses including motility, invasion, wound healing and tissue regeneration. It has been established that aberrant activation of c-Met plays a critical role in the development and progression of primary tumors and secondary metastases. HGF has the ability to dissociate epithelial sheets and to stimulate cell motility and invasion through extracellular matrix substrates, and HGF production correlates with tumor metastasis in vivo.

As shown above, (−)-trans-3-(5,6-dihydro-4H-pyrrolo[3,2,1-ij]quinolin-1-yl)-4-(1H-indol-3-yl)pyrrolidine-2,5-dione inhibited the invasive phenotype of MDA-MB-231 breast cancer cells with an estimated $IC_{50}$ value of approximately 500 nM. Similar results were seen with brain and lung cancer cells. That is, the results show that (−)-trans-3-(5,6-dihydro-4H-pyrrolo[3,2,1-ij]quinolin-1-yl)-4-(1H-indol-3-yl)pyrrolidine-2,5-dione inhibits metastatic cancer cell invasion.

Example 22

Figure 8:
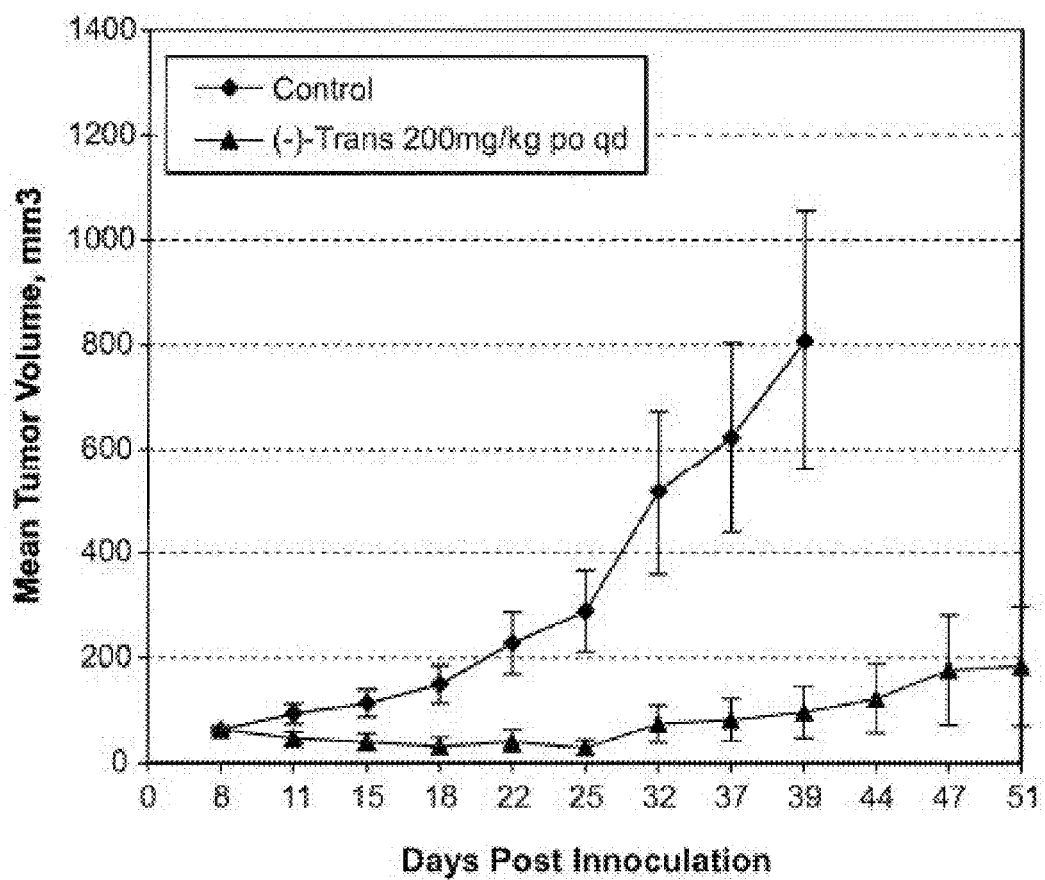
FIG. 8 sets forth an effect of (−)-trans-3-(5,6-dihydro-4H-pyrrolo[3,2,1-ij]quinolin-1-yl)-4-(1H-indol-3-yl)pyrrolidine-2,5-dione on breast cancer xenograft model.

(−)-trans-3-(5,6-dihydro-4H-pyrrolo[3,2,1-ij]quinolin-1-yl)-4-(1H-indol-3-yl)pyrrolidine-2,5-dione shows efficacy in a human breast cancer xenograft. MDA-MB-231 human breast cancer cells were inoculated subcutaneously into female athymic nude mice ($8.0 \times 10^6$ cells/mouse) and allowed to form palpable tumors. Once the tumors reached approximately 60 mm³, the animals were treated orally with (−)-trans-3-(5,6-dihydro-4H-pyrrolo[3,2,1-ij]quinolin-1-yl)-4-(1H-indol-3-yl)pyrrolidine-2,5-dione at 200 mg/kg or vehicle control daily (5 consecutive days, followed by a 2 day dosing holiday). (−)-trans-3-(5,6-dihydro-4H-pyrrolo[3,2,1-ij]quinolin-1-yl)-4-(1H-indol-3-yl)pyrrolidine-2,5-dione was formulated in PEG 400:20% Vitamin E TPGS (60:40). The animals received a total of 20 doses of (−)-trans-3-(5,6-dihydro-4H-pyrrolo[3,2,1-ij]quinolin-1-yl)-4-(1H-indol-3-yl)pyrrolidine-2,5-dione or vehicle control. Tumors were measured throughout treatment and the post-treatment observation period. Each point represents the mean±SEM of ten tumors. (See, FIG. 8)

Treatment with (−)-trans-3-(5,6-dihydro-4H-pyrrolo[3,2,1-ij]quinolin-1-yl)-4-(1H-indol-3-yl)pyrrolidine-2,5-dione as monotherapy was effective at slowing tumor growth. Tumor growth inhibition of (−)-trans-3-(5,6-dihydro-4H-pyrrolo[3,2,1-ij]quinolin-1-yl)-4-(1H-indol-3-yl)pyrrolidine-2,5-dione was calculated to be 79% and was statistically significant (p=0.009). There was no significant change in body weight due to oral administration of the vehicle or (−)-trans-3-(5,6-dihydro-4H-pyrrolo[3,2,1-ij]quinolin-1-yl)-4-(1H-indol-3-yl)pyrrolidine-2,5-dione at 200 mg/kg.

Example 23

Figure 9A:
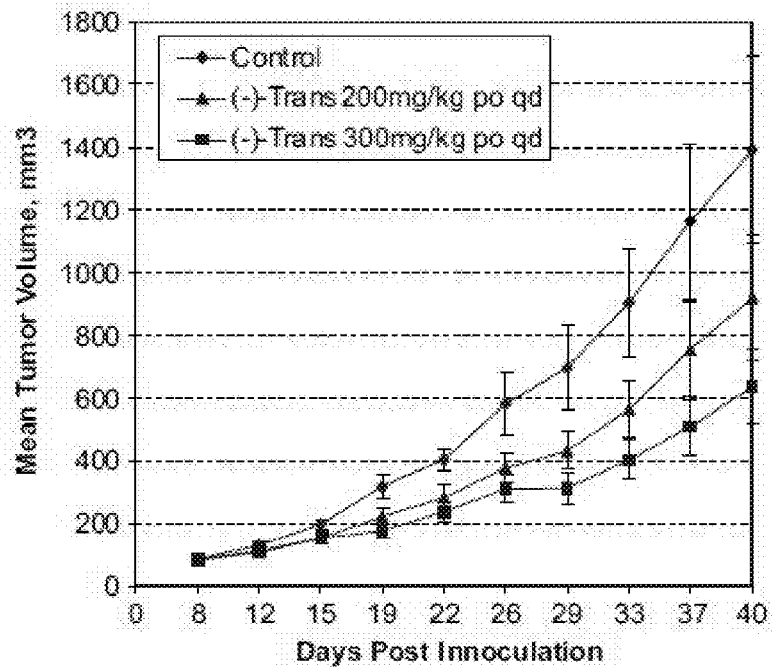
FIGS. 9A, 9B, 9C, and 9D set forth an effect of (−)-trans-3-(5,6-dihydro-4H-pyrrolo[3,2,1-ij]quinolin-1-yl)-4-(1H-indol-3-yl)pyrrolidine-2,5-dione on human colon cancer xenograft model (FIG. 9A), human pancreatic cancer xenograft model (FIG. 9B), human prostate cancer xenograft model (FIG. 9C), and human gastric cancer xenograft model (FIG. 9D).

In a human colon cancer xenograft model HT-29 human colon cancer cells were inoculated subcutaneously into female athymic nude mice ($5 \times 10^6$ cells/mouse) and allowed to form palpable tumors. Once the tumors reached approximately 60 mm³, the animals were treated orally with either (−)-trans-3-(5,6-dihydro-4H-pyrrolo[3,2,1-ij]quinolin-1-yl)-4-(1H-indol-3-yl)pyrrolidine-2,5-dione at 200 mg/kg or 300 mg/kg, or vehicle control daily (5 consecutive days, followed by a 2 day dosing holiday). (−)-trans-3-(5,6-dihydro-4H-pyrrolo[3,2,1-ij]quinolin-1-yl)-4-(1H-indol-3-yl)pyrrolidine-2,5-dione was formulated in PEG 400:20% Vitamin E TPGS (60:40). The animals received a total of 20 treatments of either (−)-trans-3-(5,6-dihydro-4H-pyrrolo[3,2,1-ij]quinolin-1-yl)-4-(1H-indol-3-yl)pyrrolidine-2,5-dione or vehicle control. Tumors were measured throughout treatment and the post-treatment observation period. Each point represents the mean±SEM of ten tumors. (See, FIG. 9A).

In this highly aggressive colon xenograft model, animals dosed with either 200 mg/kg or 300 mg/kg as a monotherapy showed significant tumor growth inhibition, with 300 mg/kg being more efficacious than 200 mg/kg. (−)-trans-3-(5,6-dihydro-4H-pyrrolo[3,2,1-ij]quinolin-1-yl)-4-(1H-indol-3-yl)pyrrolidine-2,5-dione dosed at 200 mg/kg showed an optimal tumor growth inhibition of 39% (p=0.006), while 300 mg/kg showed an optimal tumor growth inhibition of 55% (p=0.00001). There was no significant change in body weight due to oral administration of either vehicle control or (−)-trans-3-(5,6-dihydro-4H-pyrrolo[3,2,1-ij]quinolin-1-yl)-4-(1H-indol-3-yl)pyrrolidine-2,5-dione at 200 mg/kg or 300 mg/kg.

Figure 9B:
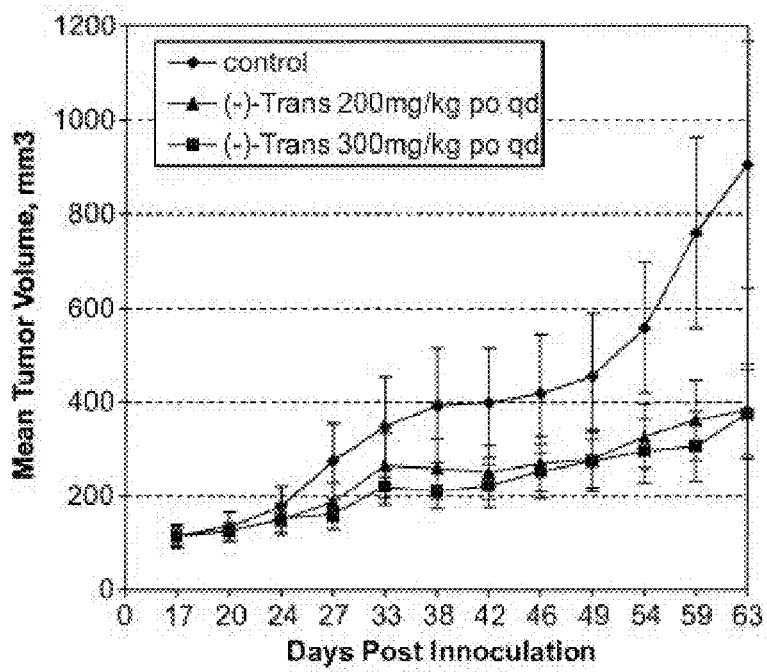
Figure 9C:
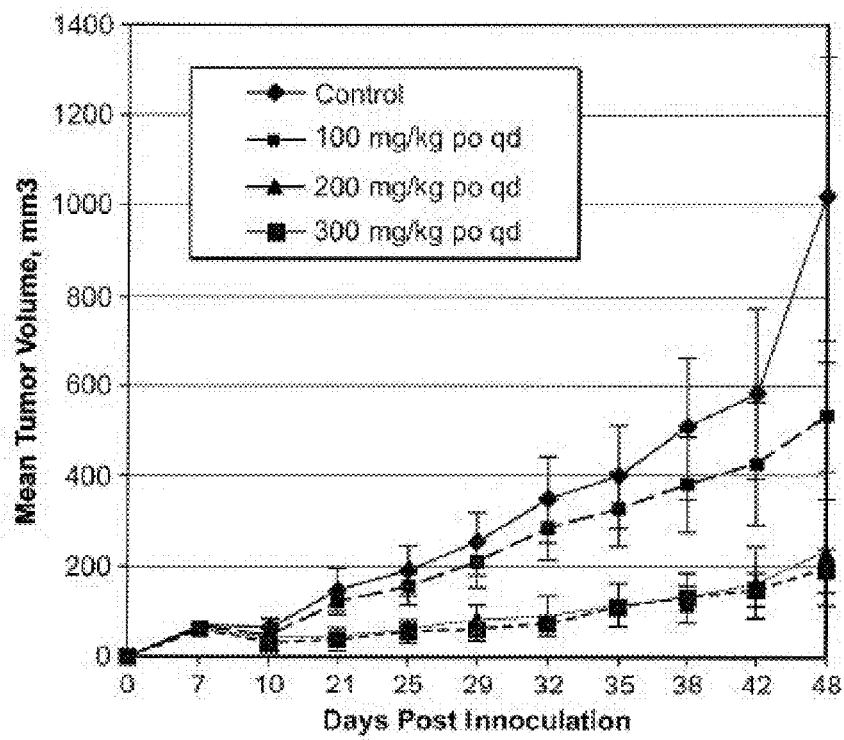
Figure 9D:
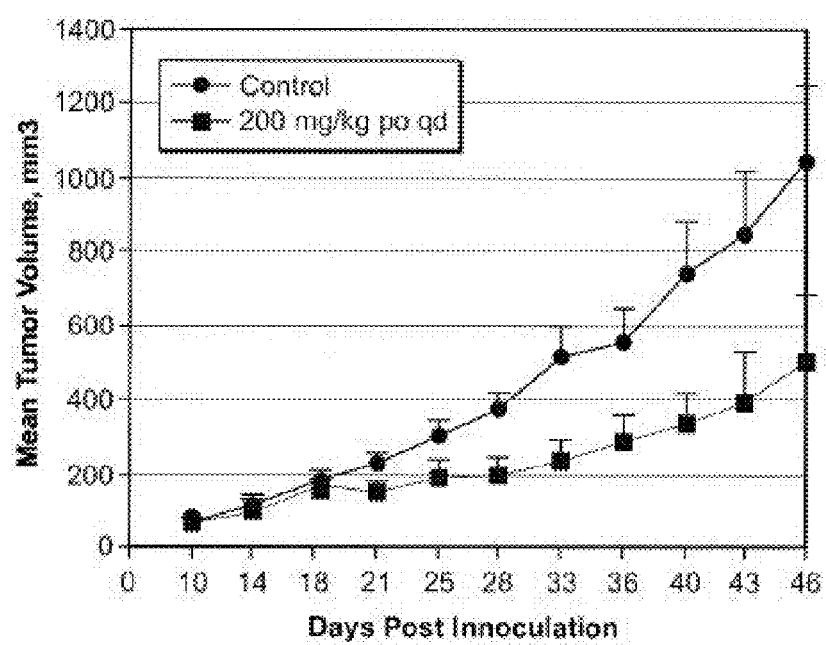

The efficacy of (−)-trans-3-(5,6-dihydro-4H-pyrrolo[3,2,1-ij]quinolin-1-yl)-4-(1H-indol-3-yl)pyrrolidine-2,5-dione was also tested in xenograft models with several other cancer cell lines: human pancreatic cancer MIA PaCa2 (FIG. 9B), human prostate cancer PC3 (FIG. 9C) and human gastric cancer MKN45 (FIG. 9D). The cells were treated with (−)-trans-3-(5,6-dihydro-4H-pyrrolo[3,2,1-ij]quinolin-1-yl)-4-(1H-indol-3-yl)pyrrolidine-2,5-dione as a monotherapy at indicated concentrations. In all these models, (−)-trans-3-(5,6-dihydro-4H-pyrrolo[3,2,1-ij]quinolin-1-yl)-4-(1H-indol-3-yl)pyrrolidine-2,5-dione significantly inhibited tumor growth.

Example 24

Figure 10:
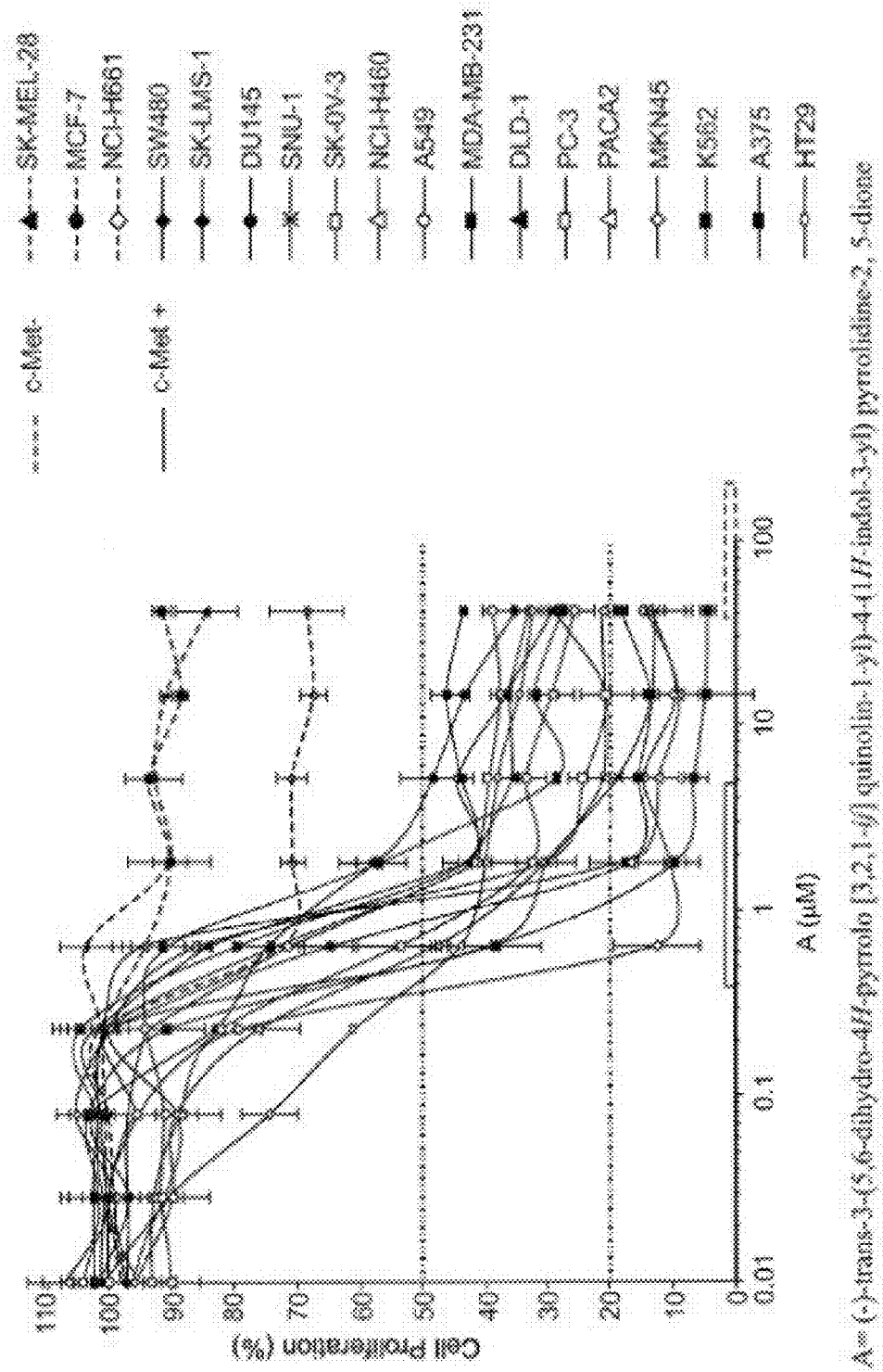
FIG. 10 sets forth cytotoxic sensitivity of multiple cell lines to (−)-trans-3-(5,6-dihydro-4H-pyrrolo[3,2,1-ij]quinolin-1-yl)-4-(1H-indol-3-yl)pyrrolidine-2,5-dione.

(−)-trans-3-(5,6-dihydro-4H-pyrrolo[3,2,1-ij]quinolin-1-yl)-4-(1H-indol-3-yl)pyrrolidine-2,5-dione showed significant cytotoxicity against multiple cancer cell lines. Various cancer cell lines were treated with (−)-trans-3-(5,6-dihydro-4H-pyrrolo[3,2,1-ij]quinolin-1-yl)-4-(1H-indol-3-yl)pyrrolidine-2,5-dione at indicated concentrations ranging from 0.03 to 30 µM. The sensitivity of these cells to (−)-trans-3-(5,6-dihydro-4H-pyrrolo[3,2,1-ij]quinolin-1-yl)-4-(1H-indol-3-yl)pyrrolidine-2,5-dione was measured by a standard cytotoxicity MTS assay (FIG. 10). Human cancer cell lines expressing c-Met and/or phospho-c-Met were sensitive to (−)-trans-3-(5,6-dihydro-4H-pyrrolo[3,2,1-ij]quinolin-1-yl)-4-(1H-indol-3-yl)pyrrolidine-2,5-dione. In contrast, human cancer cell lines with no immunodetectable c-Met or phospho-c-Met (FIG. 10, SK-MEL-28, MCF-7 and NCI-H661) showed little sensitivity.

Example 25

(−)-trans-3-(5,6-dihydro-4H-pyrrolo[3,2,1-ij]quinolin-1-yl)-4-(1H-indol-3-yl)pyrrolidine-2,5-dione was assessed for its activity to inhibit a large panel (n=230) of human kinases. The data shown in Table 2 demonstrated that (−)-trans-3-(5,6-dihydro-4H-pyrrolo[3,2,1-ij]quinolin-1-yl)-4-(1H-indol-3-yl)pyrrolidine-2,5-dione inhibited only c-Met to a significant degree and demonstrated modest activity against a small number of other kinases. (−)-trans-3-(5,6-dihydro-4H-pyrrolo[3,2,1-ij]quinolin-1-yl)-4-(1H-indol-3-yl)pyrrolidine-2,5-dione showed an inhibitory constant ($K_i$) of ~360 nM against c-Met.

TABLE 2

| Kinase | $IC_{50}$ |
|---|---|
| CAMKIIδ | ~10 μM |
| Flt4 | ~16 μM |
| PAK3 | ~6.6 μM |
| Pim-1 | 10 μM (33% inhibition) |

Example 26

Figure 11A:
FIGS. 11A and 11B set forth reduction in the amount of phosphorylated c-Met in histopathological samples treated with (−)-trans-3-(5,6-dihydro-4H-pyrrolo[3,2,1-ij]quinolin-1-yl)-4-(1H-indol-3-yl)pyrrolidine-2,5-dione by immunohistochemstry (FIG. 11A) or by Western blotting (FIG. 11B).
Figure 11B:
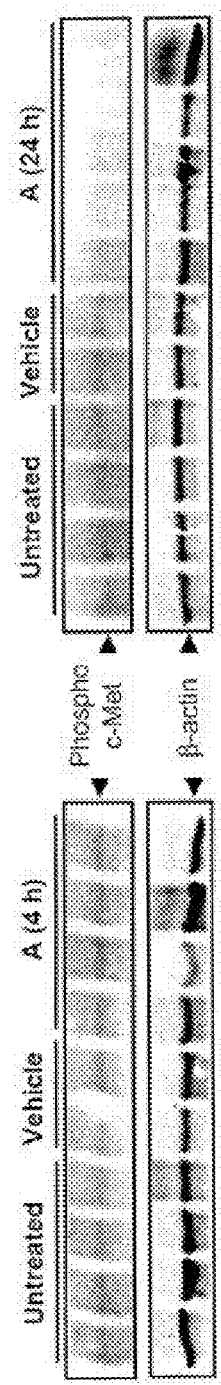
Figure 12A:
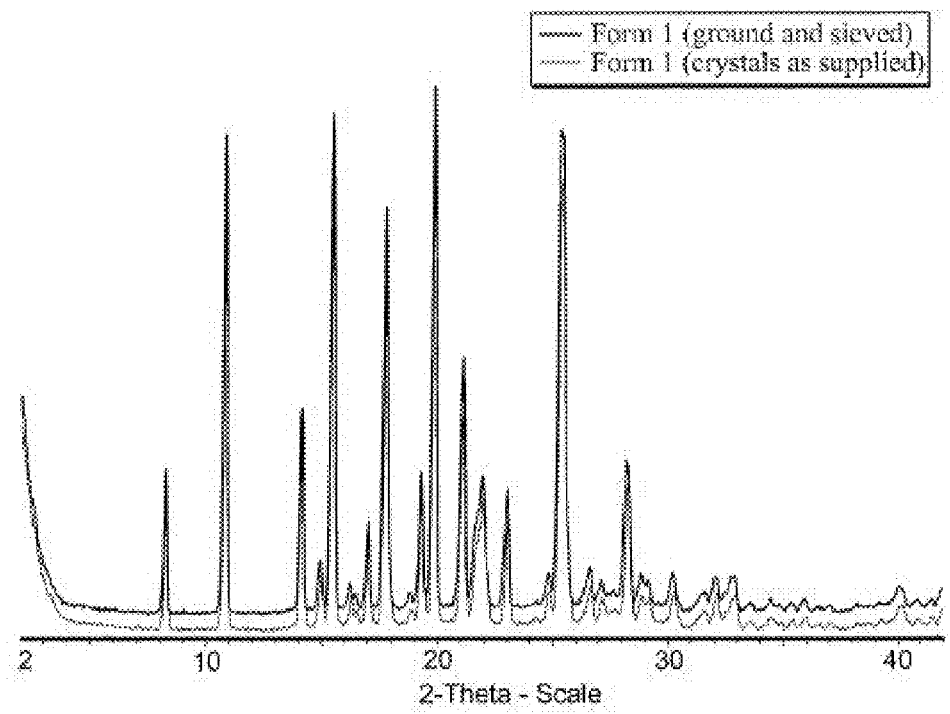
FIGS. 12A and 12B set forth the XRPD pattern of Form 1 polymorph of (−)-trans-3-(5,6-dihydro-4H-pyrrolo[3,2,1-ij]quinolin-1-yl)-4-(1H-indol-3-yl)pyrrolidine-2,5-dione (FIG. 12A); and typical 2θ values of the XRPD pattern of Form 1 polymorph of (−)-trans-3-(5,6-dihydro-4H-pyrrolo[3,2,1-ij]quinolin-1-yl)-4-(1H-indol-3-yl)pyrrolidine-2,5-dione (FIG. 12B).
Figure 12B:
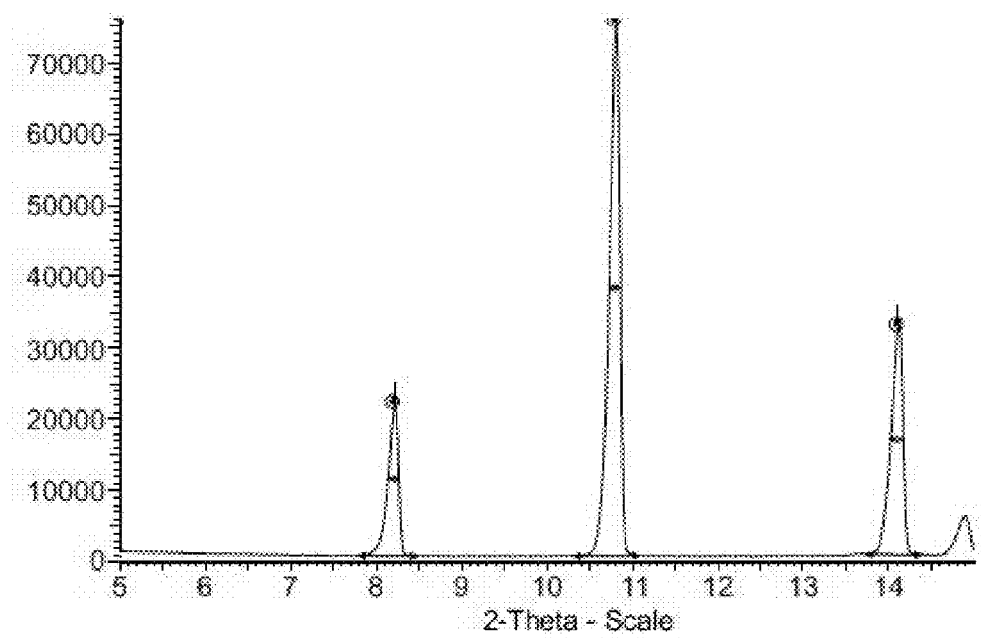
Figure 13A:
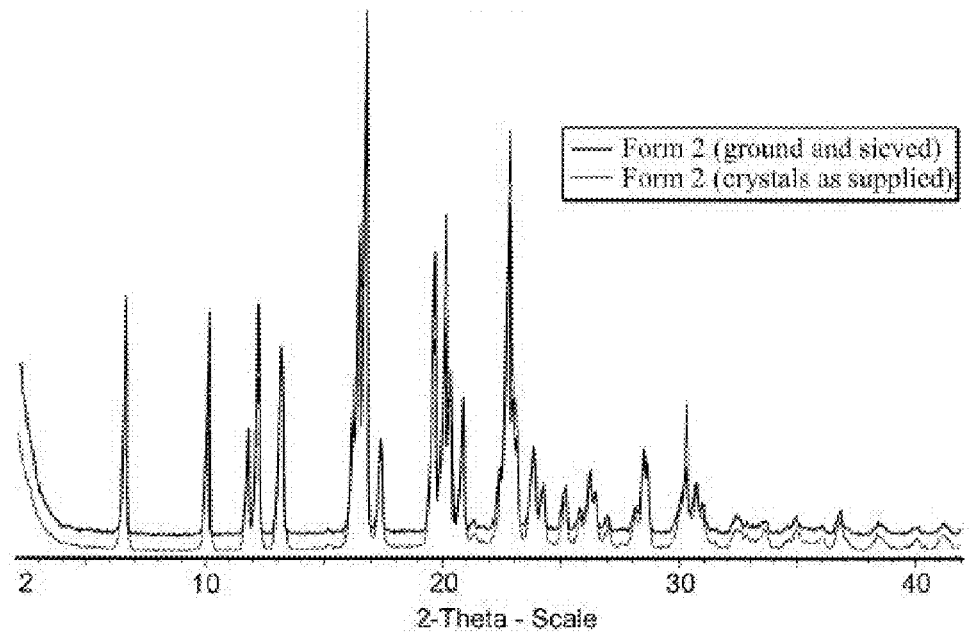
FIGS. 13A and 13B set forth the XRPD pattern of Form 2 polymorph of (−)-trans-3-(5,6-dihydro-4H-pyrrolo[3,2,1-ij]quinolin-1-yl)-4-(1H-indol-3-yl)pyrrolidine-2,5-dione (FIG. 13A); and typical 2θ values of the XRPD pattern of Form 2 polymorph of (−)-trans-3-(5,6-dihydro-4H-pyrrolo[3,2,1-ij]quinolin-1-yl)-4-(1H-indol-3-yl)pyrrolidine-2,5-dione (FIG. 13B).
Figure 13B:
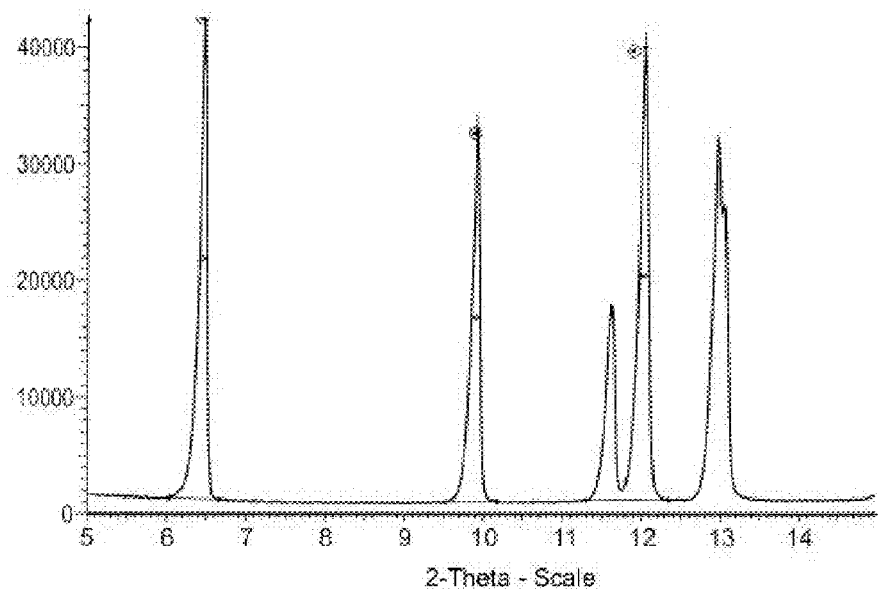

A human colon cancer xenograft model with HT-29 human colon cancer cells was established as described in Example 23. The tumor-bearing mice were treated with a single dose of (−)-trans-3-(5,6-dihydro-4H-pyrrolo[3,2,1-ij]quinolin-1-yl)-4-(1H-indol-3-yl)pyrrolidine-2,5-dione (300 mg/kg). The reduction of phospho-c-Met was detected immunohistochemically 24 hours later. A significant decrease in the amount of phospho-c-Met was visualized with the use of an immunoperoxidase system employing diaminobenzidine, which yields an insoluble brown reaction product (FIG. 11A). Western blotting of the tumor sample for phospho-c-Met confirmed the immunohistochemical analysis (FIG. 11B).

Example 27

The present example describes the inhibition of c-Met Receptor Tyrosine Kinase in Clear Cell Sarcoma and MiT (Microphthalmia Transcription Factor)-Associated Tumors. Compounds of the invention also demonstrated efficacy in a patient with clear cell sarcoma. The studies described in the present example used (−)-trans-3-(5,6-dihydro-4H-pyrrolo[3,2,1-ij]quinolin-1-yl)-4-(1H-indol-3-yl)pyrrolidine-2,5-dione, a small molecule inhibitor of the c-Met receptor tyrosine kinase.

(−)-trans-3-(5,6-dihydro-4H-pyrrolo[3,2,1-ij]quinolin-1-yl)-4-(1H-indol-3-yl)pyrrolidine-2,5-dione is a selective inhibitor of c-Met, a receptor tyrosine kinase. When abnormally activated, c-Met plays multiple roles in aspects of human cancer, including cancer cell growth, survival, angiogenesis, invasion and metastasis. The data described above demonstrate that (−)-trans-3-(5,6-dihydro-4H-pyrrolo[3,2,1-ij]quinolin-1-yl)-4-(1H-indol-3-yl)pyrrolidine-2,5-dione inhibits c-Met activation in a wide range of human tumor cell lines, including clear cell sarcoma, and show anti-tumor activity against several human tumor xenografts. In clinical studies, treatment with (−)-trans-3-(5,6-dihydro-4H-pyrrolo[3,2,1-ij]quinolin-1-yl)-4-(1H-indol-3-yl)pyrrolidine-2,5-dione has been well tolerated and has resulted in tumor responses and prolonged stable disease across broad ranges of tumors and doses.

(−)-trans-3-(5,6-dihydro-4H-pyrrolo[3,2,1-ij]quinolin-1-yl)-4-(1H-indol-3-yl)pyrrolidine-2,5-dione was administered to a patient with clear cell sarcoma. In particular, (−)-trans-3-(5,6-dihydro-4H-pyrrolo[3,2,1-ij]quinolin-1-yl)-4-(1H-indol-3-yl)pyrrolidine-2,5-dione demonstrated a partial response, as defined by RECIST (Response Evaluation Criteria in Solid Tumors), in a patient with clear cell sarcoma.

The objective response to (−)-trans-3-(5,6-dihydro-4H-pyrrolo[3,2,1-ij]quinolin-1-yl)-4-(1H-indol-3-yl)pyrrolidine-2,5-dione administration was seen in a cohort of patients affected by a molecularly-linked group of sarcoma tumor types for which there is no effective treatment.

Based on this response, (−)-trans-3-(5,6-dihydro-4H-pyrrolo[3,2,1-ij]quinolin-1-yl)-4-(1H-indol-3-yl)pyrrolidine-2,5-dione is administered at a dose of 360 milligrams (mg) twice daily (b.i.d.).

(−)-trans-3-(5,6-dihydro-4H-pyrrolo[3,2,1-ij]quinolin-1-yl)-4-(1H-indol-3-yl)pyrrolidine-2,5-dione is administered to patients with MiT (Microphthalmia Transcription Factor)-associated tumors. MiT tumors, which can include clear cell sarcoma (CCS), alveolar soft part sarcoma (ASPS) and translocation-associated renal cell carcinoma (RCC), are linked biologically through a common chromosomal abnormality that is responsible for the over-expression of c-Met resulting in the development of these tumors. Tumors with this abnormality are resistant to current therapies and, in the absence of successful surgical resection, are invariably fatal.

During the first stage of a study, 23 patients were enrolled and treated with 120 mg of (−)-trans-3-(5,6-dihydro-4H-pyrrolo[3,2,1-ij]quinolin-1-yl)-4-(1H-indol-3-yl)pyrrolidine-2,5-dione b.i.d. Fourteen of these patients were shown to be evaluable for efficacy. In addition to the patient with the confirmed partial response, ten of the evaluable patients have demonstrated stable disease.

The objective clinical response demonstrated for (−)-trans-3-(5,6-dihydro-4H-pyrrolo[3,2,1-ij]quinolin-1-yl)-4-(1H-indol-3-yl)pyrrolidine-2,5-dione builds upon the data which showed that knockout of MiT expression by shRNA suppressed c-Met expression and impeded the growth of human clear cell sarcoma cells in vitro and in vivo. This finding led to the development of a clinical trial in patients with MiT-associated tumors using (−)-trans-3-(5,6-dihydro-4H-pyrrolo[3,2,1-ij]quinolin-1-yl)-4-(1H-indol-3-yl)pyrrolidine-2,5-dione, which has shown anti-cancer activity, including objective tumor responses, as well as the ability to inhibit the c-Met protein in tumor biopsies from patients treated with the drug.

What is claimed is:

1. A (±)-trans-3-(5,6-dihydro-4H-pyrrolo[3,2,1-ij]quinolin-1-yl)-4-(1H-indol-3-yl) pyrrolidine-2,5-dione dichloromethane solvate.

2. A composition comprising (±)-trans-3-(5,6-dihydro-4H-pyrrolo[3,2,1-ij]quinolin-1-yl)-4-(1H-indol-3-yl) pyrrolidine-2,5-dione dichloromethane solvate.

3. The composition of claim 2 comprising greater than 90% (±)-trans-3-(5,6-dihydro-4H-pyrrolo[3,2,1-ij]quinolin-1-yl)-4-(1H-indol-3-yl) pyrrolidine-2,5-dione dichloromethane solvate.

4. The composition of claim 3 comprising greater than 95% (±)-trans-3-(5,6-dihydro-4H-pyrrolo[3,2,1-ij]quinolin-1-yl)-4-(1H-indol-3-yl) pyrrolidine-2,5-dione dichloromethane solvate.

5. The composition of claim 4 comprising greater than 99% (±)-trans-3-(5,6-dihydro-4H-pyrrolo[3,2,1-ij]quinolin-1-yl)-4-(1H-indol-3-yl) pyrrolidine-2,5-dione dichloromethane solvate.

* * * * *